US006191171B1

(12) United States Patent
DeLaszlo et al.

(10) Patent No.: US 6,191,171 B1
(45) Date of Patent: Feb. 20, 2001

(54) PARA-AMINOMETHYLARYL CARBOXAMIDE DERIVATIVES

(75) Inventors: Stephen E. DeLaszlo, Rumson; William K. Hagmann, Westfield, both of NJ (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/191,489

(22) Filed: Nov. 13, 1998

Related U.S. Application Data

(60) Provisional application No. 60/066,228, filed on Nov. 20, 1997.

(51) Int. Cl.[7] .................................................. A61K 31/165
(52) U.S. Cl. .................... 514/617; 514/579; 514/613; 514/620; 514/649; 514/650; 546/224; 558/23; 558/70; 558/302; 560/51; 562/125; 562/405; 562/430; 562/439; 562/442; 562/443; 568/9; 568/303
(58) Field of Search .................................. 562/430, 125, 562/405, 439, 442, 443; 546/224; 514/579, 613, 617, 620, 649, 650; 560/51; 558/23, 70, 302; 568/9, 303

(56) References Cited

U.S. PATENT DOCUMENTS

| 5,039,805 | 8/1991 | Alig et al. ........................... 546/224 |
|---|---|---|
| 5,510,332 | 4/1996 | Kogan et al. ......................... 514/14 |

FOREIGN PATENT DOCUMENTS

| WO 95/12611 | 5/1995 | (WO) . |
|---|---|---|
| WO 95/15973 | 6/1995 | (WO) . |
| WO 96/01644 | 1/1996 | (WO) . |
| WO 96/06108 | 2/1996 | (WO) . |
| WO 96/20216 | 7/1996 | (WO) . |
| WO 96/22966 | 8/1996 | (WO) . |
| WO 96/31206 | 10/1996 | (WO) . |
| WO 96/40781 | 12/1996 | (WO) . |
| WO 97/02289 | 1/1997 | (WO) . |
| WO 97/03094 | 1/1997 | (WO) . |

OTHER PUBLICATIONS

Shroff, Hitesh N., et als. Bioorganic & Medicinal Chemistry Letters vol. 6; No. 21 pp. 2495–2500 (1996).
Jackson, David Y. et als. Med. Chem., 40 pp. 3359–3368 (1997).

*Primary Examiner*—Paul J. Killos
*Assistant Examiner*—Taylor V Oh
(74) *Attorney, Agent, or Firm*—Mollie M. Yang; David L. Rose

(57) ABSTRACT para-Aminomethylaryl carboxamides of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

14 Claims, No Drawings

PARA-AMINOMETHYLARYL CARBOXAMIDE DERIVATIVES

CROSS REFERENCE TO RELATED APPLICATIONS

This application is based on, and claims priority from, U.S. provisional application No. 60/066,228 filed Nov. 20, 1997, which is hereby incorporated by reference in its entirety.

BACKGROUND OF THE INVENTION

The present invention relates to novel p-aminomethylaryl carboxamide derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selecting, integrins, cadherins and immunoglobulins. CAMs play an essential role in both normal and pathophysiological processes. Therefore, the targetting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of $\alpha$ and $\beta$ heterodimeric, transmembrane receptor molecules found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14,195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, N.Y., 1996, p. 191).

VLA-4 ("very late antigen-4"; CD49d/CD29; or $\alpha_4\beta_1$) is an integrin expressed on all leukocytes, except platelets and mature neutrophils, and is a key mediator of the cell-cell and cell-matrix interactions of leukocytes (see M. E. Hemler, "VIA Proteins in the Integrin Family: Structures, Functions, and Their Role on Leukocytes." Ann. Rev. Immunol. 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation and on dendritic and macrophage-like cells. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to pro-inflammatory cytokines (See A. J. H. Gearing and W. Newman, "Circulating adhesion molecules in disease.", Immunol. Today, 14, 506 (1993). The CS-1 domain is a 25 amino acid sequence that arises by alternative splicing within a region of fibronectin. (For a review, see R. O. Hynes "Fibronectins.", Springer-Velag, N.Y., 1990.) A role for VLA-4/CS-1 interactions in inflammatory conditions has been proposed (see M. J. Elices, "The integrin $\alpha_4\beta_1$ (VLA-4) as a therapeutic target" in Cell Adhesion and Human Disease, Ciba Found. Symp., John Wiley & Sons, NY, 1995, p. 79).

$\alpha_4\beta_7$ (also referred to as LPAM-1 and $\alpha_4\alpha_p$) is an integrin expressed on leukocytes and is a key mediator of leukocyte trafficking and homing in the gastrointestinal tract (see C. M. Parker et al., Proc. Natl. Acad. Sci. USA, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., Nature, 363, 461 (1993); A. Hamann et al., J. Immunol., 152, 3282 (1994)). MadCAM-1 can be induced in vitro by proinflammatory stimuli (See E. E. Sikorski et al. J. Immunol., 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VIA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." Nature, 356, 63 (1993) and E. Keszthelyi et al., "Evidence for a prolonged role of $\alpha_4$ integrin throughout active experimental allergic encephalomyelitis." Neurology, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the gunea-pig." Eur. J. Pharmacol., 282, 243 (1995)); iii) adjuvant-induced arthritis in rats as a model of inflammatory arthritis (see C. Barbadillo et al., "Anti-VLA-4 mAb prevents adjuvant arthritis in Lewis rats." Arthr. Rheuma. (Suppl.), 36 95 (1993) and D. Seiffge, "Protective effects of monoclonal antibody to VLA-4 on leukocyte adhesion and course of disease in adjuvant arthritis in rats." J. Rheumatol., 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", J. Clin. Invest., 93, 1700 (1994), A. Jakubowski et al., "Vascular cell adhesion molecule-Ig fusion protein selectively targets activated $\alpha$4-integrin receptors in vivo: Inhibition of autoimmune diabetes in an adoptive transfer model in nonobese diabetic mice." J. Immunol., 155, 938 (1995), and X. D. Yang et al., "Involvement of beta 7 integrin and mucosal addressin cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA-4 monoclonal antibodies on cardiac allograft survival and response to soluble antigens in mice.", Tranplant. Proc., 26, 867 (1994) and S. Molossi et al., "Blockade of very late antigen-4 integrin binding to fibronectin with connecting segment-1 peptide reduces accelerated coronary arteriopathy in rabbit cardiac allografts." J. Clin Invest., 95, 2601 (1995)); vi) spontaneous chronic colitis in cotton-top tamarins which resembles human ulcerative colitis, a form of inflammatory bowel disease (see D. K. Podolsky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin α-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7 185 (1995)); x) experimental autoimmune thyroiditis (see R. W. McMurray et al., "The role of α4 integrin and intercellular adhesion molecule-1 (ICAM-1) in murine experimental autoimmune thyroiditis." *Autoimmunity*, 23, 9 (1996); and xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996)). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; atherosclerotic plaque formation; restenosis; and circulatory shock (for examples, see A. A. Postigo et al., "The $\alpha_4\beta_1$/VCAM-1 adhesion pathway in physiology and disease.", *Res. Immunol.*, 144,723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89,375 (1996)).

At present, there is a humanized monoclonal antibody (Antegren® Athena Neurosciences/Elan ) against VLA-4 in clinical development for the treatment of "flares" associated with multiple sclerosis and a humanized monoclonal antibody (ACT-1® LeukoSite) against $\alpha_4\alpha_7$ in clinical development for the treatment of inflammatory bowel disease. Several peptidyl antagonists of VLA-4 have been described (D. Y. Jackson et al., "Potent α4α1 peptide antagonists as potential anti-inflammatory agents", *J. Med. Chem.*, 40, 3359 (1997); H. N. Shroff et al., "Small peptide inhibitors of α4β7 mediated MadCAM-1 adhesion to lymphocytes", *Bioorg. Med. Chem. Lett.*, 6 2495 (1996); U.S. Pat. No. 5,510,332, WO97/03094, WO97/02289, WO96/40781, WO96/22966, WO96/20216, WO96/01644, WO96/06108, WO95/15973). There is one report of nonpeptidyl inhibitors of the ligands for α4-integrins (WO96/31206). There still remains a need for low molecular weight, specific inhibitors of VLA-4- and α4β7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and α4β7 binding and cell adhesion and activation.

SUMMARY OF THE INVENTION

The compounds of the present invention are antagonists of the VLA-4 integrin ("very late antigen-4"; CD49d/CD29; or $\alpha_4\beta_1$) and/or the α4β7 integrin (LPAM-1 and $\alpha_4\beta_p$), thereby blocking the binding of VLA-4 to its various ligands, such as VCAM-1 and regions of fibronectin and/or α4β7 to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or α4β7 binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

DETAILED DESCRIPTION OF THE INVENTION

The present invention provides novel compounds of Formula I

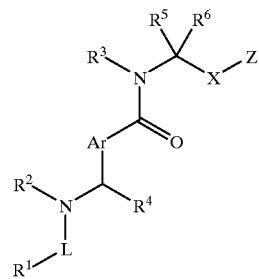

or a pharmaceutically acceptable salt thereof wherein:

Ar is
  1) optionally substituted six-membered 1,4-phenylene,
  2) optionally substituted six-membered 1,4-heteroarylene,
  3) optionally substituted six-membered 1,4-phenylene fused with a five- or six-membered aromatic, heteroaromatic, carbocyclic or heterocyclic ring,
  4) optionally substituted six-membered 1,4-heteroarylene fused with a five-or six-memberd aromatic, heteroaromatic, carbocyclic or heterocyclic ring, or
  5) optionally substituted five-membered heteroarylene having from 1–3 heteroatoms independently selected from N, O and S, wherein the substituents are one to three groups independently selected from $R^b$;

L is
  1) —C(O)—,
  2) —O—C(O)—,
  3) —NR$^e$—C(O)—,
  4) —S(O)$_2$—,
  5) —P(O)(OR$^6$)—
  6) —C(O)C(O)—.

X is
  1) a bond, or
  2) —C(R$^7$)(R$^8$)—;

Z is
  1) —C(O)OR$^d$,

2) —P(O)(OR$^d$)(OR$^e$)
3) —P(O)(R$^d$)(OR$^e$)
4) —S(O)$_m$OR$^d$,
5) —C(O)NR$^d$R$^h$, or
6) -5-tetrazolyl;

R$^1$ is
1) C$_{1-10}$alkyl,
2) C$_{2-10}$alkenyl,
3) C$_{2-10}$alkynyl,
4) Cy,
5) Cy-C$_{1-10}$alkyl,
6) Cy-C$_{2-10}$alkenyl,
7) Cy-C$_{2-10}$alkynyl, wherein alkyl, alkenyl, and alkynyl are optionally substituted with one to four substituents independently selected from R$^a$; and Cy is optionally substituted with one to four substituents independently selected from R$^b$;

R$^2$ is
1) hydrogen,
2) C$_{1-10}$ alkyl,
3) Cy,
4) Cy-C$_{1-10}$ alkyl, wherein alkyl is optionally substituted with one to four substituents independently selected from R$^a$; and Cy is optionally substituted with one to four substituents independently selected from R$^b$; or R$^2$ is joined to Ar at the ortho position to form a five or six membered heterocyclic ring containing 0–2 additional heteroatoms independently selected from oxygen, sulfur and nitrogen; said ring is optionally substituted with 1–2 groups from R$^b$.

R$^3$ is
1) hydrogen,
2) C$_{1-10}$alkyl optionally substituted with one to four substituents independently selected from R$^a$, or
3) Cy optionally substituted with one to four substituents independently selected from R$^b$, R$^4$ is
1) hydrogen,
2) a group selected from R$^1$; or R$^4$ is joined to Ar at the ortho position to form a five or six membered aromatic, heteroaromatic, carbocylic or heterocyclic, ring containing 0–2 heteroatoms independently selected from oxygen, sulfur and nitrogen; said ring is optionally substituted with 1–2 groups from Rb;

R$^5$ is
1) hydrogen,
2) C$_{1-10}$alkyl,
3) C$_{2-10}$alkenyl,
4) C$_{2-10}$alkynyl,
5) Cy-(Cy$^1$)$_p$,
6) Cy-(Cy$^1$)$_p$-C$_{1-10}$alkyl,
7) Cy-(Cy$^1$)$_p$-C$_{2-10}$alkenyl,
8) Cy-(Cy$^1$)$_p$-C$_{2-10}$alkynyl, alkyl, alkenyl and alkynyl are optionally substituted with one to four substituents independently selected from R$^a$; and Cy and Cy$^1$ are optionally substituted with one to four substituents independently selected from R$^b$;

R$^6$ is
1) hydrogen,
3) C$_{1-10}$alkyl,
4) C$_{2-10}$alkenyl,
5) C$_{2-10}$alkynyl,
6) Cy,
7) Cy-C$_{1-10}$alkyl, wherein alkyl, alkenyl and alkynyl are optionally substituted with one to four substituents selected from R$^a$, and Cy is optionally substituted with one to four substituents independently selected from R$^b$;

R$^7$ is
1) hydrogen,
2) a group selected from R$^a$, or
3) a group selected from R$^1$;

R$^8$ is
1) hydrogen,
2) C$_{1-10}$alkyl,
3) C$_{2-10}$lkenyl,
4) C$_{2-10}$alkynyl,
5) Cy,
6) Cy-C$_{1-10}$alkyl, wherein alkyl, alkenyl and alkynyl are optionally substituted with one to four substituents selected from R$^a$, and Cy is optionally substituted with one to four substituents independently selected from R$^b$.

R$^a$ is
1) —CF$_3$;
2) —OR$^d$,
3) —NO$_2$,
4) halogen
5) —S(O)$_m$R$^d$,
6) —CR$^d$(N—OR$^e$),
7) —S(O)$_2$OR$^d$,
8) —S(O)$_m$NR$^d$R$^e$,
9) —NR$^d$R$^e$,
10) —O(CR$^f$R$^g$)$_n$NR$^d$R$^e$,
11) —C(O)R$^d$,
12) —CO$_2$R$^d$,
13) —CO$_2$(CR$^f$R$^g$)$_n$CONR$^d$R$^e$,
14) —OC(O)R$^d$,
15) —CN,
16) —C(O)NR$^d$R$^e$,
17) —NR$^d$C(O)R$^e$,
18) —OC(O)NR$^d$R$^e$,
19) —NR$^d$C(O)OR$^e$, or
20) —NR$^d$C(O)NR$^d$R$^e$;

R$^b$ is
1) a group selected from R$^a$,
2) C$_{1-10}$ alkyl,
3) C$_{2-10}$ alkenyl,
4) C$_{2-10}$ alkynyl,
5) Cy, or
6) Cy-C$_{1-10}$ alkyl, wherein alkyl, alkenyl, alkynyl, and Cy are optionally substituted with a group independently selected from R$^c$; substituted with a group independently selected from R$^c$;

R$^c$ is
1) halogen,
2) amino,
3) carboxy,
4) C$_{1-4}$alkyl,
5) C$_{1-4}$alkoxy,
6) aryl,
7) aryl C$_{1-4}$alkyl, or
8) aryloxy;

R$^d$ and R$^e$ are independently selected from the group consisting of
1) hydrogen,
2) C$_{1-10}$alkyl,
3) C$_{2-10}$alkenyl,
4) C$_{2-10}$alkynyl,
5) Cy, and
6) Cy C$_{1-10}$alkyl, wherein alkyl, alkenyl, alkynyl and Cy is optionally substituted with one to four substituents independently selected from R$^c$; or $R^d$ and $R^e$ together with the atoms to which they are attached form a heterocyclic ring of 5 to 7 members containing 0–2 additional heteroatoms independently selected from oxygen, sulfur and nitrogen; $R^f$ and $R^g$ are independently selected from hydrogen, $C_{1-10}$alkyl, Cy and Cy $C_{1-10}$alkyl; or $R^f$ and $R^g$ together with the carbon to which they are attached form a ring of 5 to 7 members containing 0–2 heteroatoms independently selected from oxygen, sulfur and nitrogen;

$R^h$ is
 1) hydrogen,
 2) $C_{1-10}$alkyl,
 3) $C_{2-10}$alkenyl,
 4) $C_{2-10}$alkynyl,
 5) cyano,
 6) aryl,
 7) aryl $C_{1-10}$alkyl,
 8) heteroaryl,
 9) heteroaryl $C_{1-10}$alkyl, or
 10) —$SO_2R^i$;

wherein alkyl, alkenyl, and alkynyl are optionally substituted with one to four substituents independently selected from $R^a$; and aryl and heteroaryl are each optionally substituted with one to four substituents independently selected from $R^b$;

$R^i$
 1) $C_{1-10}$alkyl,
 2) $C_{2-10}$alkenyl,
 3) $C_{2-10}$alkynyl, or
 4) aryl;

wherein alkyl, alkenyl, alkynyl and aryl are each optionally substituted with one to four substituents independently selected from $R^c$;

Cy and $Cy^1$ are independently cycloalkyl, heterocyclyl, aryl, or heteroaryl;

m is 0, 1 or 2;

n is an integer from 1 to 10; and p is 0 or 1.

A subset of compounds of formula I are compounds wherein $R^1$ is Cy or Cy-$C_{1-10}$alkyl wherin alkyl and Cy are optionally substituted as provided above. For the purpose of $R^1$ Cy is preferably aryl optionally substituted with one or two substituents independently selected from $R^b$.

Another subset of compounds of formula I are compounds wherein Ar is optionally substituted 1,4-phenylene.

Another subset of compounds of formula I are compounds wherein L is $SO_2$ or $C(O)$.

In another subset of formula I Z is $C(O)OR^d$.

A preferred embodiment of compounds of formula I are compounds of formula Ia:

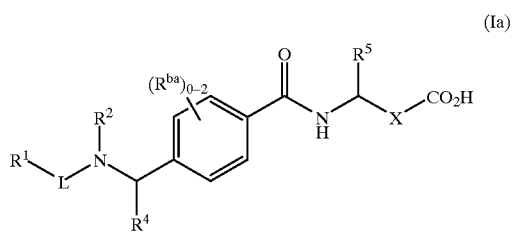

(Ia)

wherein
 L is
  1) —C(O)— or
  2) —S(O)$_2$;

X is
 1) abond or
 2) $C(R^7)(R^8)$;

$R^1$ is
 2) Cy, or
 2) Cy-$C_{1-10}$alkyl, wherein alkyl is optionally substituted with one to four substituents independently selected from $R^a$; and Cy is optionally substituted with one to four substituents independently selected from $R^b$;

$R^2$ is
 1) H or
 2) $C_{1-5}$alkyl;

$R^3$ is
 1) H or
 2) $C_{1-5}$alkyl;

$R^5$ is
 1) $C_{1-10}$alkyl,
 2) Cy-$(Cy^1)_p$,
 3) Cy-$(Cy^1)_p$-$C_{1-10}$alkyl, wherein alkyl is optionally substituted with one to four substituents independently selected from $R^a$; and Cy and $Cy^1$ are optionally substituted with one to four substituents independently selected from $R^b$;

$R^7$ is
 1) hydrogen, or
 2) $C_{1-3}$alkyl;

$R^8$ is
 1) hydrogen;

$R^{ba}$ is
 1) halogen,
 2) $C_{1-3}$alkyl, or
 3) $C_{1-3}$alkoxy;

all the other variables are as defined above under formula I.

In another preferred embodiment compounds having the formula Ib are provided:

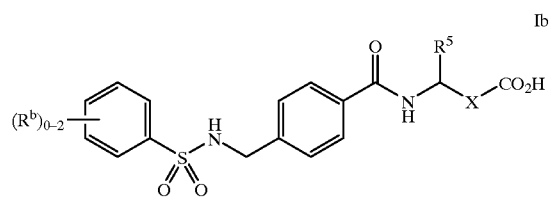

Ib wherein
 X is
  1) a bond, or
  2) $CH_2$;

$R^5$ is
  1) $C_{1-5}$alkyl,
  2) Cy-$(Cy^1)_p$,
  3) Cy-$(Cy^1)_p$-$C_{1-3}$alkyl, wherein Cy and $Cy^1$ are optionally substituted with one to two substituents independently selected from $R^b$;

Cy and $Cy^1$ are independently aryl or heteroaryl;

$R^b$ is as defined above under formula I.

In another preferred embodiment compounds having the formula Ic:

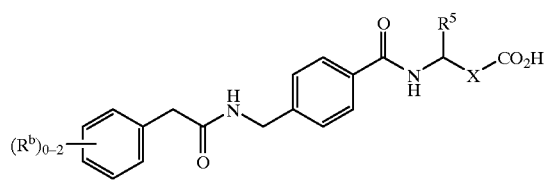

Ic wherein

X is
1) a bond, or
2) $CH_2$;

$R^5$ is
1) $C_{1-5}$alkyl,
2) $Cy-(Cy^1)_p$,
3) $Cy-(Cy^1)_p-C_{1-3}$alkyl, wherein Cy and $Cy^1$ are optionally substituted with one to two substituents independently selected from $R^b$;

Cy and $Cy^1$ are independently aryl or heteroaryl;

$R^b$ is as defined above under formula I.

Representative compounds of the present invention include the following:

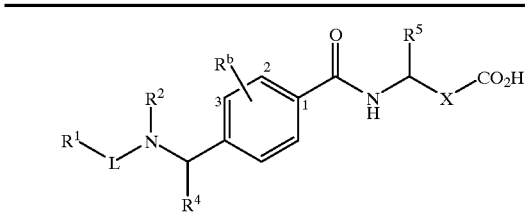

| Ex | $R^1$—L | $R^5$ | X |
|---|---|---|---|
| $R^2=R^b=R^4=H$ | | | |
| 1 | 2-MPUPA[a] | n-butyl | — |
| 2 | 2-MPUPA | benzyl | — |
| 3 | 2-MPUPA | phenyl* | — |
| 4 | 2-MPUPA | 4-biphenylmethyl | — |
| 5 | 2-MPUPA | methyl* | $CH_2$ |
| 6 | 2-MPUPA | benzyl* | $CH_2$ |
| 7 | 2-MPUPA | isobutyl* | $CH_2$ |
| 8 | 2-MPUPA | phenyl* | $CH_2$ |
| 9 | 2-MPUPA | H | CH($CH_3$)* |
| 10 | 3,5-(diCl)—Ph—$SO_2$ | n-butyl | — |
| 11 | 3,5-(diCl)—Ph—$SO_2$ | benzyl | — |
| 12 | 3,5-(diCl)—Ph—$SO_2$ | phenyl* | — |
| 13 | 3,5-(diCl)—Ph—$SO_2$ | 4-biphenylmethyl | — |
| 14 | 3,5-(diCl)—Ph—$SO_2$ | phenyl* | $CH_2$ |
| 15 | 3,5-(diCl)—Ph—$SO_2$ | benzyl* | $CH_2$ |
| 16 | 3,5-(diCl)—Ph—$SO_2$ | isobuty*l | $CH_2$ |
| 17 | 3,5-(diCl)—Ph—$SO_2$ | benzyl# | — |
| 18 | benzoyl | 4-biphenylmethyl | — |
| 19 | phenylacetyl | 4-biphenylmethyl | — |
| 20 | 3,5-(diCl)-benzoyl | 4-biphenylmethyl | — |
| 21 | n-BU—$SO_2$ | 4-biphenylmethyl | — |
| 22 | 3-(CN)—Ph—$SO_2$ | 4-biphenylmethyl | — |
| 23 | 3-(F)—Ph—$SO_2$ | 4-biphenylmethyl | — |
| 24 | 4-(OMe)—Ph—$SO_2$ | 4-biphenylmethyl | — |
| 25 | 3-($CF_3$)—Ph—$SO_2$ | 4-biphenylmethyl | — |
| 26 | 3-(Cl)—Ph—$SO_2$ | 4-biphenylmethyl | — |
| 27 | Ph—$SO_2$ | 4-biphenylmethyl | — |
| 28 | 4-(F)—Ph—$SO_2$ | 4-biphenylmethyl | — |
| 29 | 3-(Me)—Ph—$SO_2$ | 4-biphenylmethyl | — |
| 30 | 3,4-(di$CF_3$)—Ph—$SO_2$ | 4-biphenylmethyl | — |
| 31 | 4-(O$CF_3$)—Ph—$SO_2$ | 4-biphenylmethyl | — |

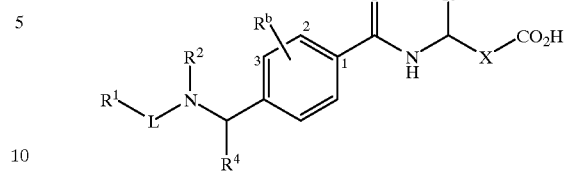

-continued

| Ex | $R^1$—L | $R^5$ | X |
|---|---|---|---|
| 32 | 1-Me-4-imidazolyl—$SO_2$ | 4-biphenylmethyl | — |
| 33 | 4-(Cl)—Ph—$SO_2$ | 4-biphenylmethyl | — |
| 34 | 3,4-(diCl)—Ph—$SO_2$ | 4-biphenylmethyl | — |
| 35 | 2,3,4-(triF)-Ph—$SO_2$ | 4-biphenylmethyl | — |
| 36 | 2-(Cl)—Ph—$SO_2$ | 4-biphenylmethyl | — |
| 37 | 3-(Cl)-4-(F)—Ph—$SO_2$ | 4-biphenylmethyl | — |
| 38 | 2-thienyl-$SO_2$ | 4-biphenylmethyl | — |
| 39 | 2-(COOH)—Ph—$SO_2$ | 4-biphenylmethyl | — |
| 40 | 5-(Cl)-2-thienyl-$SO_2$ | 4-biphenylmethyl | — |
| 41 | 3,5-(diCl)—Ph—CO— | 4-biphenylmethyl | — |
| 43 | 3,5-(diCl)—Ph—$SO_2$ | 4-fluorobenzyl | — |
| 44 | 3-F—Ph—$SO_2$ | 4-fluorobenzyl | — |
| 45 | 3,5-(diCl)—Ph—$SO_2$ | 4-iodobenzyl | — |
| 46 | 3,5-(diCl)—Ph—$SO_2$ | 2'-cyanobiphenyl-methyl | — |
| 47 | 3,5-(diCl)—Ph—$SO_2$ | 2'-methoxybiphenylmethyl | — |
| 48 | 3,5-(diCl)—Ph—$SO_2$ | 4'-t-butylbiphenylmethyl | — |
| 49 | 3,5-(diCl)—Ph—$SO_2$ | 3'-methoxybiphenylmethyl | — |
| 50 | 3,5-(diCl)—Ph—$SO_2$ | 4'-methoxybiphenylmethyl | — |
| 51 | 3,5-(diCl)—Ph—$SO_2$ | 4'-methylthiobiphenylmethyl | — |
| 52 | 3,5-(diCl)—Ph—$SO_2$ | 2'-formylbiphenylmethyl | — |
| 53 | 3,5-(diCl)—Ph—$SO_2$ | 3'-acetamidobiphenylmethyl | — |
| 54 | 3,5-(diCl)—Ph—$SO_2$ | 4-(2-thienyl)benzyl | — |
| 55 | 3,5-(diCl)—Ph—$SO_2$ | 4-(3-chloro-2-thienyl)benzyl | — |
| 56 | 3,5-(diCl)—Ph—$SO_2$ | 4-(3-thienyl)benzyl | — |
| 57 | 3,5-(diCl)—Ph—$SO_2$ | 4-(2-naphthyl)benzyl | — |
| 58 | 3,5-(diCl)—Ph—$SO_2$ | 2'-cyanobiphenylmethyl (D isomer) | — |
| 63 | 3,5-(diCl)—Ph—$SO_2$ | 4-(3-methyl-1,2,4-oxadiazol-5-yl)benzyl | — |
| 66 | 3,5-(diCl)—Ph—$SO_2$ | 4-(1-pyrrolidinecarbonyloxy)-benzyl | — |
| 67 | 3,5-(diCl)—Ph—$SO_2$ | 4-(2-ethoxyethoxy)benzyl | — |
| 68 | 3,5-(diCl)—Ph—$SO_2$ | 4-(t-butoxycarbonyloxy)-benzyl | — |
| 69 | 3,5-(diCl)—Ph—$SO_2$ | 4-(t-butoxy)benzyl | — |
| $R^b=R^4=H; R^2=CH_3$ | | | |
| 42 | 3,5-(diCl)—Ph—$SO_2$ | 4-biphenylmethyl | — |
| $R^2=R^4=H; R^b=$3-F (Ex. 59), 3-OMe (Ex. 61), 2-Me (Ex. 62 | | | |
| 59 | 3,5-(diCl)—Ph—$SO_2$ | 4-biphenylmethyl | — |
| 61 | 3,5-(diCl)—Ph—$SO_2$ | 4-biphenylmethyl | — |
| 62 | 3,5-(diCl)—Ph—$SO_2$ | 4-biphenylmethyl | — |
| $R^2=R^b=H; R^4=CH_3$ | | | |
| 64 | 3,5-(diCl)—Ph—$SO_2$ | 4-biphenylmethyl | — |
| 65 | 3,5-(diCl)—Ph—$SO_2$ | 2'-methoxybiphenylmethyl | — |
| 70 | 3-CN—Ph$SO_2$ | 2'-cyanobiphenylmethyl | — |

[a]2-MPUPA = 4-(N'-(2-methylphenyl)ureido)phenylacetyl

EX 60

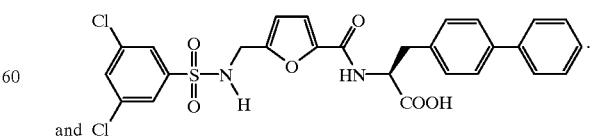

and

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic ring fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"1,4-Heteroarylene" means a bivalent monocyclic heteroaryl group in which the two substituents are para to each other, and the numbers do not necessarily refer to the normal numbering of the ring system.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O each of said ring having from 3 to 10 atoms. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benz oxazinyl, tetrahydrohydroquinolinyl, tetrahydroisoquinolinyl, dihydroindolyl, and the like.

"Halogen" includes fluorine, chlorine, bromine and iodine.

The following abbreviations are used:

| BOC (boc) | t-butyloxycarbonyl |
| calc. | calculated |
| CBZ (Cbz) | benzyloxycarbonyl |
| DBU | 1,8-diazabicyclo[5.4.0]undec-7-ene |
| DCC | dicyclohexylcarbodiimide |
| DIEA | diisopropylethylamine |
| DMAP | 4-(N,N-dimethylamino)pyridine |
| DMF | dimethylformamide |
| DMSO | dimethylsulfoxide |

-continued

| EDC | 1-(3-dimethylaminopropyl)3-ethylcarbodiimide HCl |
| EtOAc | ethyl acetate |
| FAB-MS | fast atom bombardment-mass spectroscopy |
| FMOC (Fmoc) | fluororenylmethoxycarbonyl |
| HBTU | 2-(1H-benzotriazol-1-yl)-1,1,3,3-tetramethyluronium hexafluorophosphate |
| HOBt | 1-hydroxybenzottriazole hydrate |
| HPLC | high pressure liquid chromatography |
| Me | methyl |
| MHz | megahertz |
| NBS | N-bromosuccinimde |
| NMP | N-methylpyrrolidin-2-one |
| NMR | nuclear magnetic resonance |
| Ph | phenyl |
| Pr | propyl |
| prep. | prepared |
| TFA | trifluoroacetic acid |
| THF | tetrahydrofuran |
| TLC | thin-layer chromatography |
| TMAD | N,N,N',N'-tetramethylazodicarboxamide |

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine,-N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic., benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or $\alpha 4\beta 7$ integrin makes them useful for preventing or reversing the symptoms, disorders or diseases induced by the binding of VLA-4 and or $\alpha 4\beta 7$ to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or $\alpha 4\beta 7$ binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) hepatitis, and (20) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| -continued | |
|---|---|
| Tablet | mg/tablet |
| Compound of Formula I | 19 |
| Microcrystalline Cellulose | 415 |
| Povidone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973, WO96/31206 and WO98142656; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Compounds of Formuila I may be prepared via the schemes outlined below. Reaction conditions are proposed to accomplish the chemical conversions that are outlined. However, one skilled in the art of organic synthesis may find other conditions that are satisfactory for accomplishing the conversions that are suggested.

The core of Formula I is the 4-aminomethyl substituted aromatic ring F in Scheme 1. Several aminomethyl benzoic acids are commercially available (for example FMOC-(4-aminomethyl)-benzoic acid). Other aminomethyl substituted aromatic or heteroaromatic acids of Formula I may be prepared as outlined in Scheme 1. In Scheme 1 benzoic acid is exemplified; however, one skilled in the art will recognize the applicability of the reactions to other aromatic and heteroaromatic acids encompassed by the definition of Ar under formula I.

In Scheme 1,4-alkylbenzoic acid esters A is brominated in the presence of N-bromosuccinimide (NBS) and a free radical initiator such as benzoylperoxide to give the bromide B. Displacement of the bromine atom by potasium phthalimide provides C. Saponification of the ester with a base such as sodium hydroxide provides the acid D, and removal of the phthalimide protecting group with hydrazine leads to the amino acid E. $R^2$ groups may be introduced onto E by reductive alkylation with $R^2CHO$ to give I. Conversion to the FMOC protected aminomethyl benzic acid F may be achieved by treatment of E or I with FMOCCl in the presence of aqueous base. If an amine protecting group other than FMOC is required (such as t-butoxyoxycarbonyl or benzyloxycarbonyl) reagents and methods for its introduction and removal are known to those skilled in the art of organic synthesis may be used.

Alternative methods for the preparation of E and I are shown in Scheme 1a. Bromide B is treated with sodium azide in a solvent such as dimethylformamide to give G. Reduction of the azide by catalytic hydrogenation or treatment with triphenylphosphine and water provides E (R=ester). A further method of preparing E is available through reduction of 4-cyanobenzoic acids H by hydrogenation. Direct displacement of the bromine atom by a primary amine provides I.

Ketones J are readily available via palladium catalysed coupling of 4-halo benzoic acid esters (halo=bromo or iodo) or 4-hydroxybenzoic acid esters (derivatized as a triflate) and acid chlorides. Reductive alkylation with a primary amine provides I. Various conditions may be applied to accomplish the reductive alkylation reactions described herein. These include the use of reducing agents such as sodium cyanoborohydride, sodium triacetoxyborohydride and sodium cyanoborohydride. The reactions are generally performed in the presence of a week acid such as acetic acid in a solvent such as THF or dichloroethane.

Scheme 1

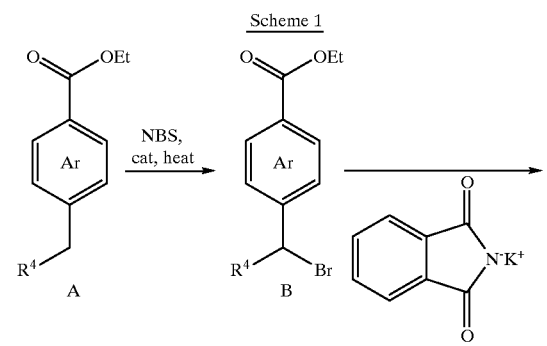

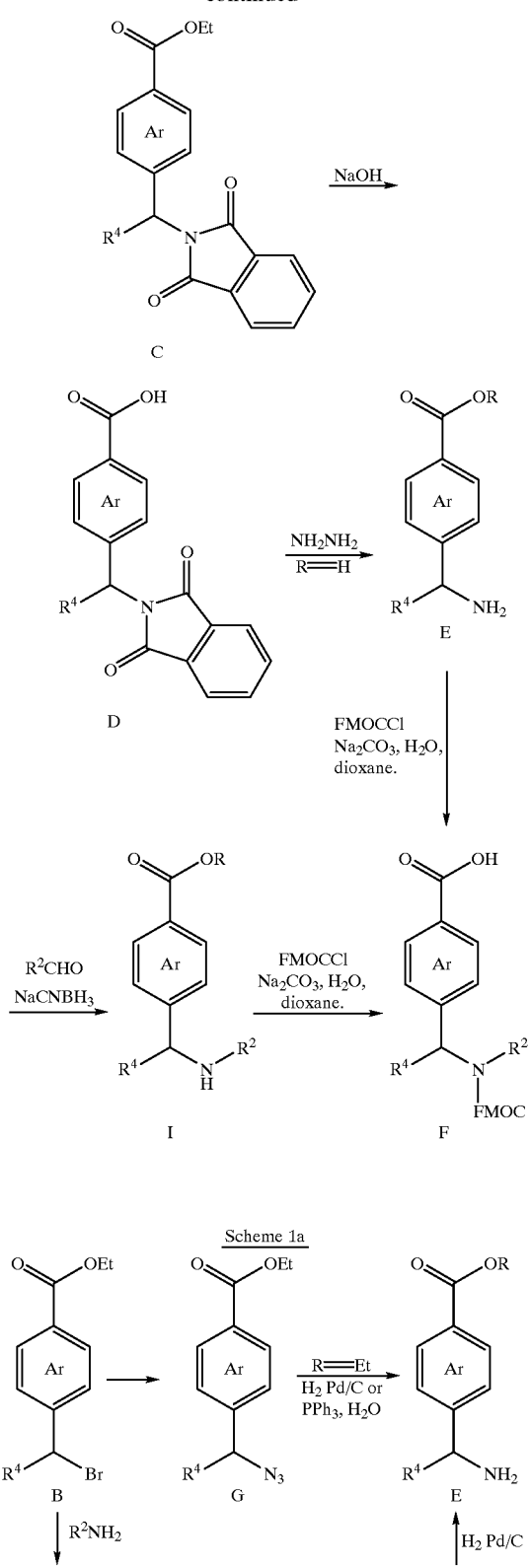

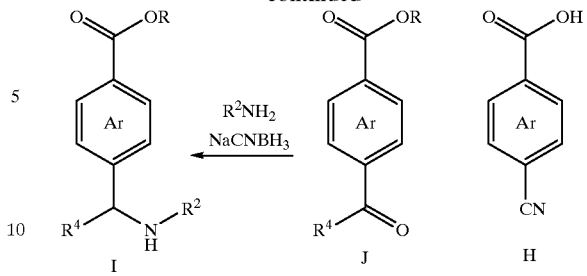

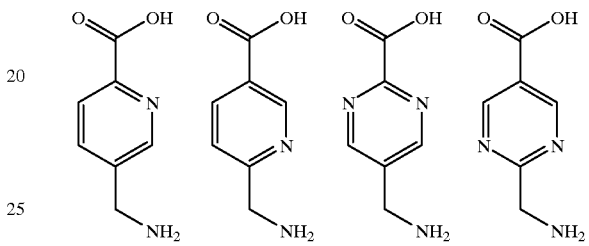

The synthesis of the following para-aminomethyl-heteroarylcarboxylic acids is disclosed in Chemistry and Pharmaceutical Bulletin 1408 1980.

These compounds can be appropriately protected and introduced into compounds of Formula I.

Compounds of the present invention may be prepared by procedures illustrated in the accompanying schemes. In the first method (Scheme 2), a resin-based synthetic strategy is outlined where the resin employed is represented by the ball ⊗ A. An N-Fmoc-protected amino acid derivative B (Fmoc=fluorenylmethoxycarbonyl) is loaded on to the appropriate handle (see below) that is attached to the resin bead using dicyclohexylcarbodiimide (DCC) or EDC and catalytic amount of DMAP in dimethylformamide (DMF), methylene chloride ($CH_2Cl_2$) or a mixture of both to give C. Handles are structures that facilitate the attachment of the amino acid to the resin but then enable the completed molecule to be cleaved from the resin as the carboxylic acid. For example handles may include, but are not limited to: 4-(4-hydroxymethyl-3-methoxyphenoxybenzoic acid, 4-hydroxymethyl-phenoxyacetic acid and 3-(4-hydroxymethylphenoxy)propionic acid all attached to an amine containing resin through the carboxylic acid as an amide.

The Fmoc protecting group on C is removed with piperidine in DMF to yield free amine D. The Fmoc-protected carboxylic acid derivative E is coupled to D employing standard peptide (in this instance, 2-(1H-benzotriazol-1-yl)-1,1,3,3-tetramethyluronium hexafluoro-phosphate (HBTU), HOBt, and N,N-diisopropylethylamine (DIEA) in DMF to yield dipeptoid F. The Fmoc group is removed with piperidine in DMF to yield the free amine G. The amine is then derivatized with the appropriate $R^1L$ group by sulfonylation or acylation to give H as indicated on the scheme. The product of this reaction may in itself, be converted further to other $R^1$ groups by utilization of functional group interconversions well known to one skilled in the art. For example, in the case of L=SO2 the nitrogen atom may be alkylated by an alkyl halide or under Mitsonobu conditions with an alcohol to give I. The final product is removed from the resin with strong acid (in this instance, trifluoroacetic acid (TFA) in the presence, or absence (depending on the sensitivity of the product) of thioanisole and dithiane to yield compounds of the present invention of formula I.
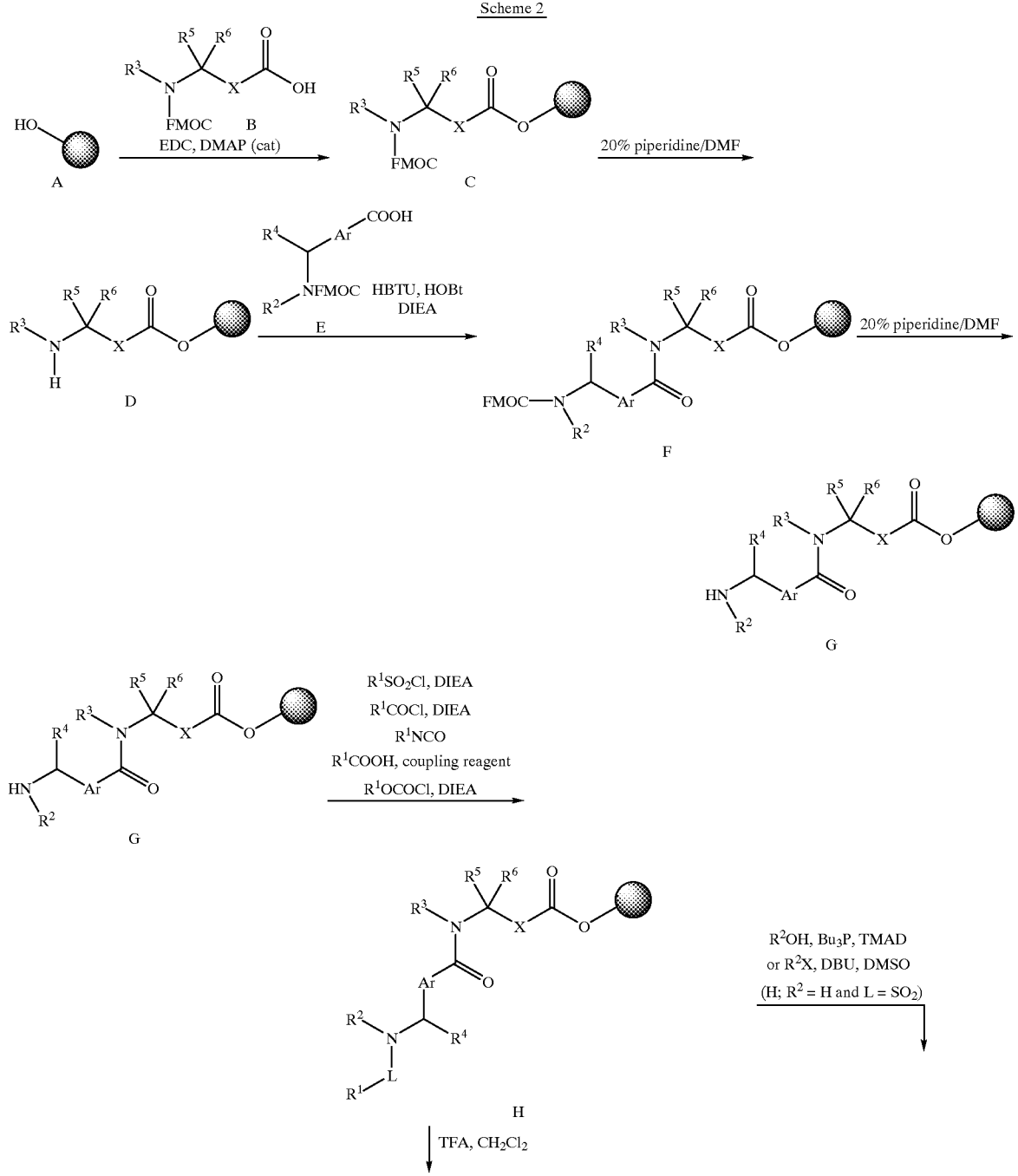
Scheme 2

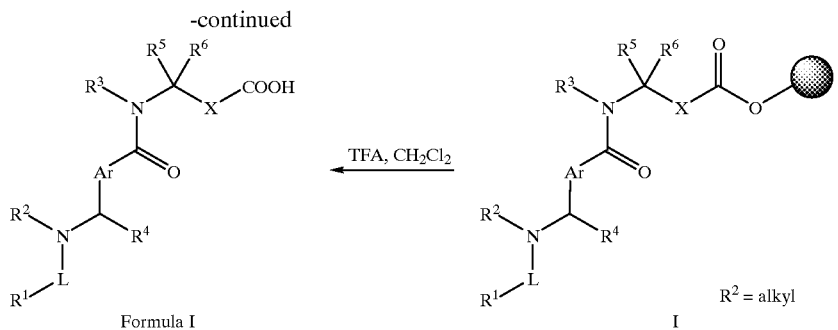

In the second method (Scheme 3), standard solution phase synthetic methodology is outlined. Although a t-butyl ester is indicated in the synthesis other alkyl esters may be used. An N-protected amino acid derivative A (Boc=tert-butyloxycarbonyl) is treated with tert-butyl 2,2,2-trichloroacetimidate in the presence of boron trifluoride etherate or isobutylene in the presence of acid to yield tert-butyl ester B. The use of an N-unprotected amino acid in reaction with isobutylene and acid may provide C directly. B is deprotected (in the case of Z=Boc, FMOC or Cbz) and the product, C, is coupled to an N-protected aminomethyl-benzoic acid derivative D to yield dipeptide E. Removal of the N-protecting group Z yields F. The amine is then derivatized with the appropriate $R^1L$ group by sulfonylation or acylation as indicated on the scheme to provide G. The product of this reaction may in itself, be converted further to other $R^1$ groups by utilization of functional group interconversions well known to one skilled in the art. For example, in the case of L=SO2 the nitrogen atom may be alkylated by an alkyl halide or under Mitsonobu conditions with an alcohol to give H. The final product is prepared by acid catalysed removal of the t-butyl ester by treatment with an acid such as TFA.

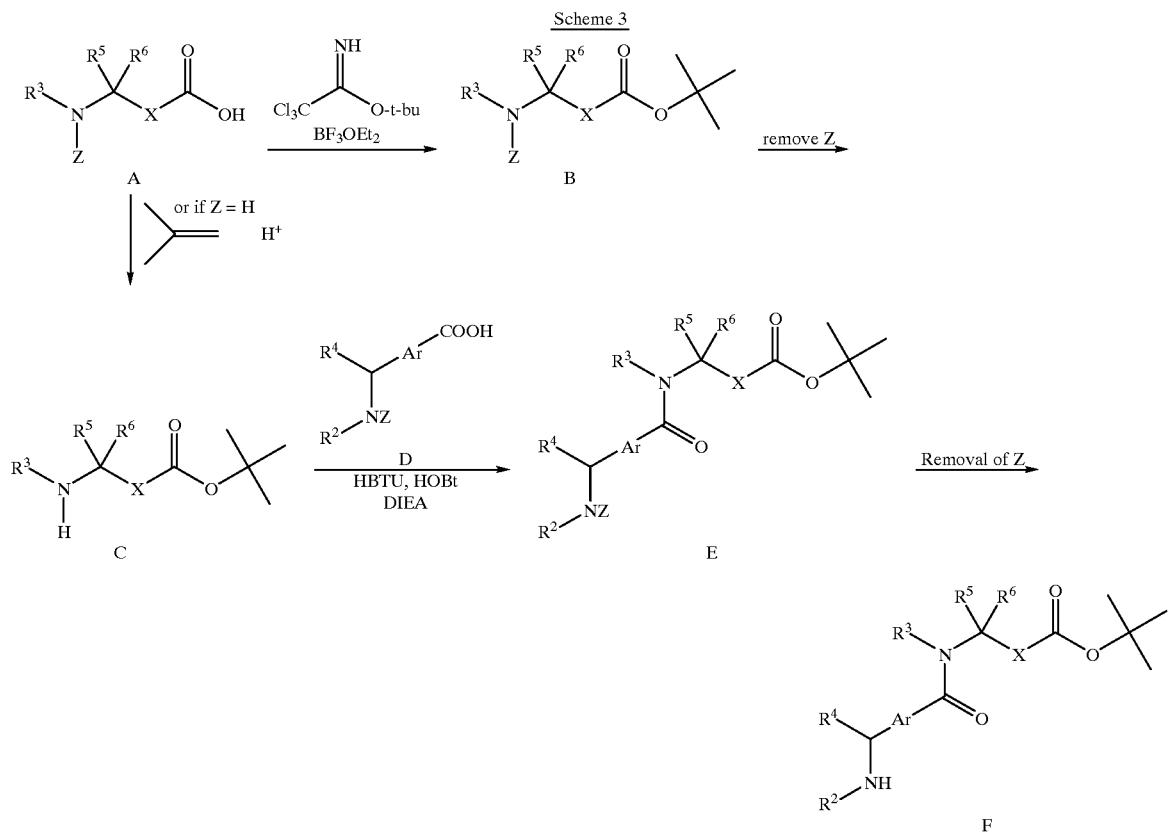

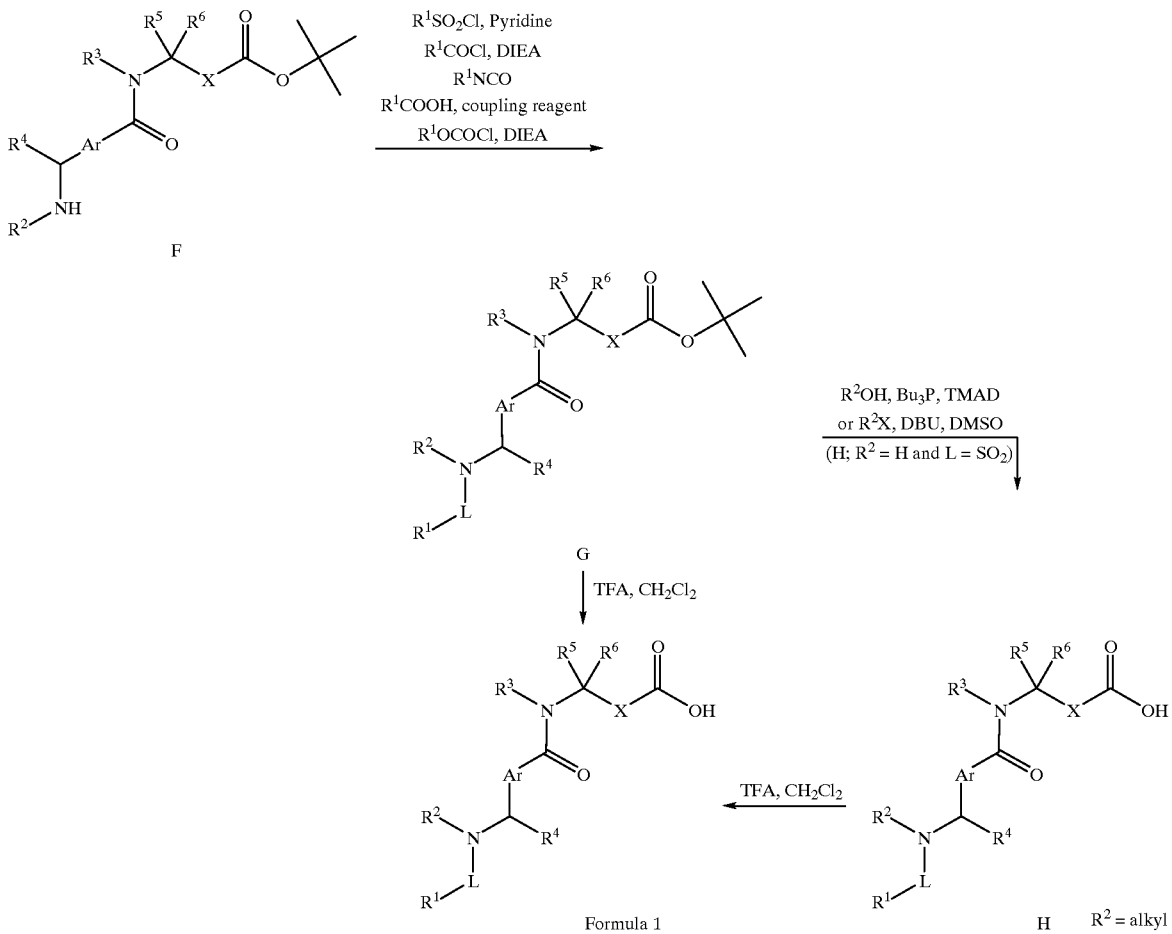

Z = CBz, FMOC, BOC. Removal by: hydrogenation (H$_2$, 10% Pd/C, 20% Et$_2$NH/DMF, HCl/EtOAc respectively.

Compounds wherein biaryl (includes aryl-heteroaryl groups) groups are present may be prepared as outlined in Scheme 4. Note that although this scheme is specfic for compounds wherein R$^5$ has the biaryl unit, the chemistry may be applied whenever a biaryl group is necessary. Substituted aryl or heteroaryl boronic acids are coupled to A in the presence of a palladium(0) reagent, such as tetrakis (triphenyl-phosphine)palladium under Suzuki conditions (N. Miyaura et al., *Synth. Commun.,* 1981, 11, 513–519) to yieldB. Tyrosine triflate starting materials are prepared by treatment of the tyrosine analog of A with triflic anhydride in pyridine. The carboxylic acid protecting group is then removed to give the corresponding compounds of Formula I. If the aryl or heteroaryl boronic acid is not commercially available, but the corresponding bromide or iodide is, then the bromide or iodide can be converted into the desired boronic acid by treatment with an alkyllithium reagent in tetrahydrofuran at low temperature followed by addition of trimethyl or triisopropyl borate. Hydrolysis to the boronic acid can be effected by treatment of the intermediate with aqueous base and then acid. Aryl boronates which may also be utilized in coupling reactions in place of aryl boronic acids may be prepared by palladium catalyzed boronation of aryl iodides and bromides as decribed in J. Org Chem, 1995,60, 7508–7510.

Scheme 4

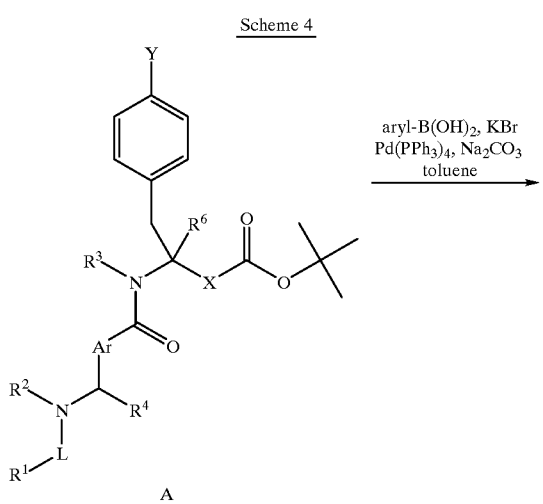

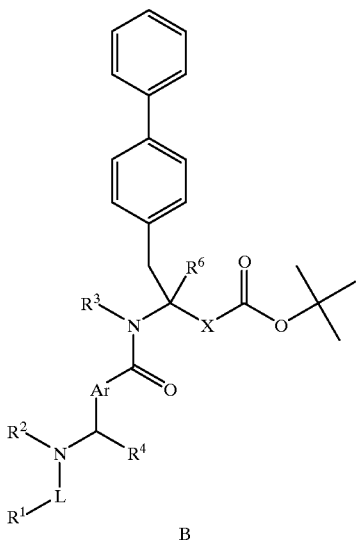

Y = Br, I, OSO₂CF₃
Aryl = heteroaryl or aryl

B

Alternatively, the aryl coupling reaction may be performed by application of Stille-type carbon-carbon bond forming conditions (Scheme 5). (A. M. Echavarren and J. K. Stille, *J. Am. Chem. Soc.* 1987, 109, 5478–5486). The aryl bromide or iodide intermediate A is converted into its trimethyltin derivative B using hexamethylditin in the presence of palladium(0) and lithium chloride and then reacted with an appropriately substituted aryl or heteroaryl bromide, iodide, or triflate in the presence of a palladium reagent, such as tetrakis(triphenyl-phosphine)palladium(0) or tris(dibenzylideneacetone)dipalladium(0), in a suitable solvent, such as toluene, dioxane, DMF, or 1-methyl-2-pyrrolidinone, to give intermediate C. The protecting group is then removed to give compounds of Formula I. Aryl boronates may also be utilized in coupling reactions in place of aryl stannane. They may be prepared by palladium catalyzed boronation of aryl iodides and bromides as decribed in *J. Org Chem*, 1995, 60, 7508–7510. The resulting boronate may then be coupled to aryl bromide or iodide to provide C.

Scheme 5

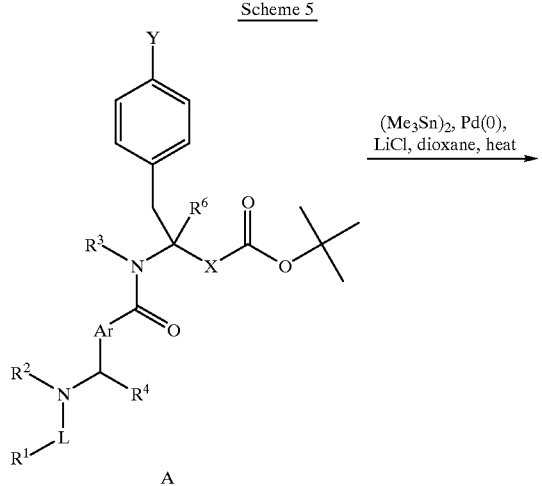

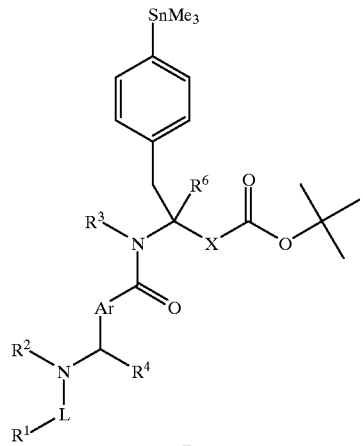

B

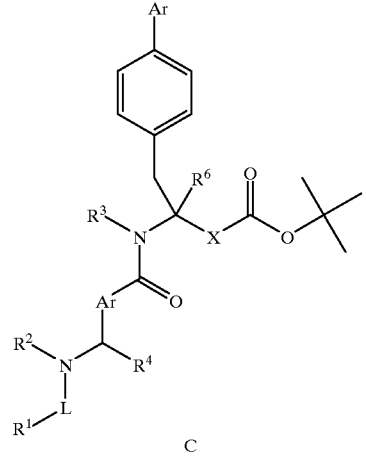

Y = Br, I, OSO₂CF₃
Ar = aryl or heteroaryl

C

PREPARATION OF AMINO ACIDS

PREPARATION 1. N-FMOC-(L)-2'-cyano-biphenylalanine

Step A. N-FMOC-(L)-4-iodophenylalanine, t-butyl ester

To a solution of 15 g (51 mmol) of (L)-4-iodophenylalanine in 100 ml of diglyme and 15 ml of concentrated H₂SO₄ was added 30 ml of condensed isobutylene. The vessel was agitated overnight and the crude product was diluted with 100 ml of ethyl acetate. The solution was added to excess sodium hydroxide solution while maintaining the temperature below 30° C. A white precipitate formed which dissolved upon addition of sodium hydroxide solution. The resulting mixture was filtered and the aqueous phase was extracted with ethyl acetate. The combined extracts were washed with brine and dried over anhydrous magnesium sulfate. The mixture was filtered and concentrated in vacuo to give a solution of the product in diglyme. The solution was diluted with 200 ml of ether and was treated with excess 1N HCl in ether with rapid stirring. The resulting precipitate was collected and dried in vacuo after washing with ether. A white solid (9.01 g) was collected of 4-iodophenylalanine t-butyl ester hydrochloride. To a suspension of 5.1 g (13.3 mmol) of the amine hydrochloride in 30 ml of methylene chloride was added 3.6 g (27 mmol) of diisopropyl ethyl amine followed by 3.43 g (0.013 g) of FMOCCl. The solution was stirred overnight at room temperature, washed with 1N HCl solution (3×50 ml), water (1×50 ml), saturated sodium carbonate solution (2×50 ml) and brine (1×50 ml). The solution was dried over MgSO$_4$, filtered and concentrated in vacuo to give 6.43 g of N-FMOC-(L)-4-iodophenylalanine, t-butyl ester as a white foam. 300 MHz $^1$H NMR (CDCl$_3$): δ1.44 (s, 9 H); 3.05 (d, 2H);4.20–4.60 (m, 4 H); 5.30 (m, 1H); 6.90 (d, 2H), 7.30–7.80 (m, 12H).

Step B. N-FMO C-(L)-4-trimethylstannylphenylalanine, t-butyl ester

In a dry 250 ml round bottom flask was added 6.20 g (10.5 mmol) of the product of Step A, 0.48 g (115 mmol) LiCl and 0.6 g (0.52 mmol) of palladium tetrakistriphenylphosphine followed by 50 ml of dry dioxane. The mixture was stirred for 5 minutes. 5.2 g (15.8 mmol) of hexamethylditin was added and the reaction mixture was degassed and then heated at 90° C. The reaction mixture gave a black suspension after 15 minutes. Completion of the conversion was determined by TLC (10% EtOAc/hexanes; sm r.f.=0.3, product r.f.=0.4). The mixture was diluted with 100 ml of hexanes and stirred to give a precipitate. The suspension was filtered through celite and concentrated in vacuo to give a gum. The residue was purified by flash chromatography over silica gel eluting with 10% EtOAc/hexanes to give 5.02 g of the stannane (77% yield). 300 MHz $^1$H NMR (CDCl$_3$): δ0.30 (s, 9 H); 1.45 (s, 9H); 3.20 (d, 2H), 4.20–4.60 (m, 4H); 5.29 (d, 1H); 7.12 (d, 2H); 7.22–7.45 (m, 6H); 7.59 (d, 2H), 7.75 (d, 2H).

Step C. N-FMOC-(L)-2'-cyano-biphenylalanine, t-butyl ester

In a clean, dry round bottom flask fitted with a reflux condenser vented through a three way valve attached to a vacuum source and nitrogen gas was added 1.56 g (6.8 mmol) of 2-iodobenzonitrile, 0.117 (0.12 mmol) of tris(dibenzylidineacetone)-dipalladium (0), 0.8 g (19 mmol) of LiCl and 0.15 g (0.5 mmol) of triphenylarsine followed by 30 ml of N-methylpyrrolidinone (NMP). The mixture was degassed and stirred for 10 minutes at which time most of the catalyst mixture had dissolved. 3.9 g (6.21 mmol) of the product of Step B was added in 10 ml of NMP and the reaction was heated to 80° C. for 90 minutes. TLC (10% EtOAc/hexanes) indicated complete consumption of stannane (rf=0.4) and formation of the desired product (rf=0.1). The solution was cooled to room temperature and diluted with 50 ml of EtOAc. The solution was stirred with 20 ml of saturated KF for 20 minutes. The mixture was diluted with 200 ml of EtOAc and washed with water (6×75 ml), brine (1×50 ml) and was dried over MgSO$_4$. The mixture was filtered and concentrated in vacuo and the residue was purified by Biotage Flash chromatography over silica gel eluting with 20% EtOAc/hexanes to give 1.91 g (54% yield) of the title compound. 300 MHz $^1$H NMR (CDCl$_3$): δ1.45 (s, 9H); 3.19 (d, 2H); 4.20–4.68 (m, 4H); 5.40 (d, 1H); 7.25–7.55 (m, 12H); 7.65 (m, 2H), 7.80 (d, 2H).

Step D. N-FMOC-(L)-2'-cyano-biphenylalanine 2.4 g of the product of Step C was treated with 50 ml of a mixture of 50% trifluoroacetic acid in methylene chloride. The reaction mixture was concentrated in vacuo. The residue was azeotropically dried by concentration from toluene to give the desired product as a foam. 300 MHz $^1$H NMR (CD$_3$OD): δ3.02 (dd, 1H); 3.30 (dd, 1H); 4.05–4.35 (m, 3H); 4.52 (m, 1H); 7.10–7.50 (m, 12H); 7.60 (m, 2H), 7.78 (d, 2H).

PREPARATION 2. N-(FMOC)-(S)-2'-methoxy-biphenylalanine

Step A. N-(Boc)-(S)-4-iodo-phenylalanine t-butyl ester

To a suspension of 7.5 g (0.019 m) of 4-iodophenylalanine t-butyl ester (see PREPARATION 1, Step A prior to treatment with HCl) in 100 ml of dichloromethane was added 2.52 g 0.019 m of diisopropyl ethyl amine followed by 4.14 g of ditertbutyldicarbonate. The reaction mixture was stirred over night at room temperature, washed with 1N HCl (2×25 ml), water (2×25 ml), saturated NaHCO$_3$ (1×25 ml), brine (1×25 ml) and was dried over MgSO$_4$. The mixture was filtered and concentrated in vacuo to give the desired product as a gum 8.8 g (100% yield). 300 MHz $^1$H NMR (CDCl$_3$): 1.39 (s, 18H); 2.98 (AB, 2H); 4.4 (dd, 2H); 5.0 bd, 1H); 6.92 (d, 2H); 7.62 (d, 2H).

Step B. N-(Boc)-(S)-2'-methoxy-biphenylalanine t-butyl ester 7.97 g (0.018 m) of the product of Step A was dissolved in 160 ml of 2:1 toluene:ethanol. To this solution was added 2.99 g (0.0198 m) 2-methoxyphenylboronic acid, 0.69 g of tetrakistriphenylphosphine palladium (0) and 22.7 ml (0.45 m) of 2.0 M sodium carbonate in water. The reaction mixture was degassed three times and then heated at 90° O for 90 minutes at which time the reaction mixture was black. The mixture was diluted with 300 ml of ethyl acetate and was washed with water (3×150 ml) and brine (2×100 ml) and was dried over MgSO$_4$. The mixture was filtered and concentrated in vacuo. The residue was purified by flash chromatography over silica gel eluting with 10% EtOAc/hexanes to give 6.89 g (88% yield) of the desired product as a white solid. 300 MHz $^1$H NMR (CDCl$_3$): 1.45 (s, 18H); 3.10 (d, 2H); 3.80 (s, 3H); 4.5 (dd, 2H); 5.1 bd, 1H); 7.0 (m, 2H); 7.22 (d, 2H); 7.30 (d, 2H); 7.49 (d, 2H); 7.62 (d, 2H).

Step C. N-(FMOC)-(S)-2'-methoxy-biphenylalanine

To a solution of 4.85 g (0.0113 m) of the product of Step B in 100 ml of t-butyl acetate was added 5.53 g (0.056 m) of concentrated sulfuric acid. The solution was stirred at room temperature for 2 hours and then carefully neutralized by addition of saturated aqueous NaHCO$_3$ solution. The solution was washed with NaHCO$_3$ solution, dried over NaSO$_4$, filtered and concentrated in vacuo. To a solution of 4.42 g of amine in 150 ml of methylene chloride was added at 0° C. 1.74 g (13.5 mmol) of diisopropylethyl amine followed by 3.48 g (13.5 mmol) of FMOCCl. The solution was stirred for 2 hours and washed with 1N HCl (3×50 ml), saturated NaHCO$_3$ solution (2×50 ml) and brine (1×50 ml). The mixture was filtered and concentrated in vacuo. The residue was purified by flash chromatography over silica gel eluting with a gradient of 10–25% EtOAc/hexanes to give 7.10 g (88% yield) of the desired product as a glass. The material was dissolved in 125 ml of 50% trifluoracetic acid/methylene chloride and stirred at room temperature for 2.5 hours. The solution was concentrated in vacuo and the residue was redissolved in toluene and concentrated in vacuo to give 7.01 g of the desired product. 96% pure by HPLC (254 nm). 300 MHz $^1$H NMR (CDCl$_3$): 3.20 (m, 2H); 3.76 (s, 3H); 4.21 (t, 1H); 4.41 (m, 4H); 4.76 (dd, 1H); 5.32 (d, 1H); 6.8–7.8 (m, 16H).

The following examples are provided to illustrate the invention and are not to be construed as limiting the scope of the invention in any manner. In the examples, biphenyl, unless otherwise specified, means 4-biphenyl.

GENERAL PROCEDURE FOR THE SOLID-PHASE SYNTHESIS OF COMPOUNDS OF FORMULA I

Preparation of N-FMOC-4-aminomethylbenzoic acid

To a solution of 1.5 grams (0.01 mol) of 4-aminomethyl benzoic acid in 26 ml of 10% Na$_2$CO$_3$ at 13 ml of dioxane at 0° C. was added a solution of fluorenylmethoxychloroformate in 20 ml of dioxane dropwise. A thick glutinous mixture formed. The mixture was stirred over night at room temperature and then diluted with 100 ml of water and was washed with EtOAc (3×20 ml). The aqueous phase was acidified with concentrated HCl added dropwise with cooling and stirring. A white precipitate formed which was collected by filtration and dried in vacuo to give desired product. $^1$H-NMR (CDCl$_3$ 300 MHz): 4.15 (t, 1H); 4.31 (d, 2H); 4.40 (d, 2H); 6.0 (t, 1H); 7.22 (t, 4H); 7.32 (t, 2H); 7.52 (d, 2H); 7.69 (d, 2H); 7.70 (d, 2H); 7.92 (d, 2H).

Step A. Loading of N-Fmoc-amino Acid Derivatives onto Resins

In general Tantagel resin (see structure below) was used. In some cases Sasrin resin (commercially available) that incorporates the same linker (of 4-hydroxymethyl-3-methoxy-phenoxybutyric acid) was used. Wang resin was also utilized successfully. The N-Fmoc-amino acids (commercially available or preloaded on resin) were loaded onto the resin previously functionalized with the appropriate linker to provide, for example in the case of Tantagel resin:

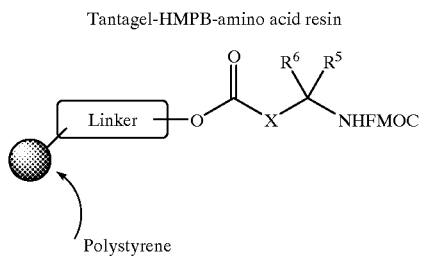

Tantagel-HMPB-amino acid resin

The resin was prepared in the following fashion (Tantagel resin used as an example): 25 grams of Tantagel amine resin (commercially available) was swollen in methylene chloride (150 ml). To this mixture was added 3.74 g of 4-hydroxymethyl-3-methoxy-phenoxybutyric acid (commercially available), 2.1 g of N-hydroxybenzotriazole (HOBt) and 1.88 g of diisopropyl carbodiimide. The mixture was stirred over night at room temperature, filtered and the residue was washed with methylene chloride (3×150 ml), MeOH (3×150 ml), methylene chloride (3×150 ml) and ether (3×100 ml). The residue was dried in vacuo to give the handle derivatized resin ready for loading with the appropriate amino acid.

The resin (2.0 g, 0.54 mmol) was swollen in 50% THF/CH$_2$Cl$_2$ and suspended in 5 ml of the same solvent. 5 mg of dimethylaminopyridine (DMAP) was added followed by 1.0 mmol of the amino acid N-protected with the fluorenyl-methoxycarbamate (FMOC) group. EDC (1.0 mmol) was added and the mixture was agitated over night. The mixture was filtered and then resubmitted to the same conditions for 4 hours. The mixture was filtered and the residue was washed (3×10 ml 50% THF/CH$_2$Cl$_2$), 3×10 ml CH$_2$Cl$_2$, 3×10 ml MeOH, 3×10 ml CH$_2$Cl$_2$, 2×10 ml ether) and dried in vacuo to give the desired product.

Step B. Deprotection of the N-Fmoc Group

The N-Fmoc protecting group was removed from the resin (75 mg, 0.015 mmol) from Step A by treatment with 20% piperidine in dimethylformamide for 30 minutes. Following filtration, the resin was washed sequentially with dimethylformamide (3 times), dichloromethane (1 time) and dimethylformamide (2 times) and used in the subsequent reaction.

Step C. Coupling of the Next N-Fmoc-amino Acid Derivative

A solution of the FMOC-4-aminomethylbenzoic acid (0.06 mmol) (for example N-FMOC-4-aminomethylbenzoic acid prepared as described above) in dimethylformamide (1 mL) was mixed with 2-(1H-benzotriazol-1-yl)-1,1,3,3-tetramethyluronium hexafluorophosphate (HBTU) (0.75 mmol), 1-N-hydroxybenztriazole (0.06 mmol) and diisopropylethylamine (0.07 mmol). This solution was transferred to resin from Step B and typically allowed to react for 2 hours. Couplings were monitored by ninhydrin reaction. The coupling mixture was filtered and the resin washed with dimethylformamide (3 times) and used in the subsequent reaction.

Step D. Deprotection of the N-Fmoc Group

The N-Fmoc protecting group was removed from the resin from Step C by the procedure described in Step B and used in the subsequent reaction.

Step E. Acylation (or Sulfonylation) of the Terminal Amino Group

Acylation: The desired N-terminal capping reagent (acylchloride) (0.06 mol) was dissolved in 50% CH$_2$Cl$_2$/THF (2 ml), mixed with N,N-diisopropylethylamine(0.8 mmol) and added to the resin from Step D. After agitating over night, the resin was sequentially washed (3×3 ml 50% THF/CH$_2$Cl$_2$), 3×3 ml CH$_2$Cl$_2$, 3×3 ml MeOH, 3×3 ml CH$_2$Cl$_2$ Sulfonylation: The desired N-terminal capping reagent (sulfonylchloride) (0.06 mol) was dissolved in 50% CH$_2$Cl$_2$/THF (2 ml), mixed with pyridine (0.8 mmol) and added to the resin from Step D. After agitating over night, the resin was sequentially washed (3×3 ml 50% THF/CH$_2$Cl$_2$), 3×3 ml CH$_2$Cl$_2$, 3×3 ml MeOH, 3×3 ml CH$_2$Cl$_2$ Step F. Acylation with Carboxylic Acid A solution of the carboxylic acid (0.06 mmol) in dimethylformamide (1 mL) was mixed with 2-(1H-benzotriazol-1-yl)-1,1,3,3-tetramethyluronium hexafluorophosphate (0.75 mmol), 1-N-hydroxybenzotriazole(0.06 mmol) and diisopropylethylamine (0.07 mmol). This solution was transferred to resin from Step D and typically allowed to react overnight. The coupling mixture was filtered and the resin washed with (3×3 ml DMF), 3×3 ml CH$_2$Cl$_2$, 3×3 ml MeOH, 3×3 ml CH$_2$Cl$_2$ Step G. Alkylation of Sulfonamide.

To a suspension of the product of Step E in 1:1 DMSO/NMP is added 6 equivalents of the alkyl halide and 6 equivalents of DBU. The resin is mixed over night, filtered and washed (3×3 ml 50% DMSO/NMP), 3×3 ml CH$_2$Cl$_2$, 3×3 ml MeOH, 3×3 ml CH$_2$Cl$_2$). The resulting product is cleaved from the resin.

Step H. Further Modifications of Product of Step E and Step F

The product of Step E and Step F may be further modified by FMOC group removal as described above and acylations of the type described in Step E and F using excess amounts of acids, sulfonyl chlorides, isocyanates (in 50% CH$_2$Cl$_2$/THF), chloroformates, and acid chlorides. Reactions are always followed by rigorous washing with the reaction solvent and subsequently CH$_2$Cl$_2$, MeOH and CH$_2$Cl$_2$ Step I. Cleavage of the Desired Products from the Resins The final desired products were cleaved from the resins from Step E-H by mixing with a solution of 5% trifluoroacetic acid in CH$_2$Cl$_2$ (3×3 ml for 10 minutes each) and filtering. The filtrate was concentrated in vacuo. The residue was dissolved in 50% CH$_3$CN/H$_2$O and lyophilised. In the case of t-butyl tyrosine and t-butyl aspartate commercially available SASRIN resins was utilised and 1% trifluoroacetic acid in CH$_2$Cl$_2$ (10×1 ml for 3 minutes) was used for cleavage. In the case of the Wang linker, 95%TFA/water was used (3×1 ml for 10 min). The eluant was run into 20% pyridine in methanol and the mixture was concentrated in vacuo. Purity was assesed by HPLC and molecular ions were obtained by electrospray ionization mass spectrometry to confirm the structure of each compound.

The following compounds were prepared by the general procedure described above using the appropriate amino acid derivatives and other reagents. In the case of amides derived from o-methyl-phenylureaphenylacetic acid, the acid used for coupling, o-methyl-phenylureaphenylacetic acid, was prepared as in International Patent Application WO 96/22966. Compounds were characterized by reverse phase HPLC, mass spectrum and $^1$H-NMR for some analogs. Mass spectral data for the sulfonamide analogs was difficult to interpret due to weak molecular ion signals. In the lists below the carbon atom to which $R^5$ is attached has the same stereo configuration as the corresponding carbon atom of the L-amino acid starting material, except when marked with *, the starting amino acid is a dl mixture, and when marked with #, the starting amino acid is a D-amino acid. 2-MPUPA is 4-(N'-(2-methylphenyl)ureido)phenylacetyl.

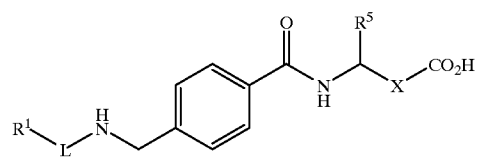

| Ex | $R^1$—L | $R^5$ | X | Observed FAB MS |
|---|---|---|---|---|
| 1 | 2-MPUPA | n-butyl | — | 531 ($M^+$ + 1) |
|   |   |   |   | 548 ($M^+$ + 18) |
| 2 | 2-MPUPA | benzyl | — | 565 ($M^+$ + 1) |
|   |   |   |   | 582 ($M^+$ + 18) |
| 3 | 2-MPUPA | phenyl* | — | 551 ($M^+$ + 1) |
|   |   |   |   | 568 ($M^+$ + 18) |
| 4 | 2-MPUPA | 4-biphenylmethyl | — | 641 ($M^+$ + 1) |
|   |   |   |   | 658 ($M^+$ + 18) |
| 5 | 2-MPUPA | methyl* | $CH_2$ | 503 ($M^+$ + 1) |
|   |   |   |   | 520 ($M^+$ + 18) |
| 6 | 2-MPUPA | benzyl* | $CH_2$ | 579 ($M^+$ + 1) |
|   |   |   |   | 596 ($M^+$ + 18) |
| 7 | 2-MPUPA | isobutyl* | $CH_2$ | 545 ($M^+$ + 1) |
|   |   |   |   | 562 ($M^+$ + 18) |
| 8 | 2-MPUPA | phenyl* | $CH_2$ | 565 ($M^+$ + 1) |
|   |   |   |   | 582 ($M^+$ + 18) |
| 9 | 2-MPUPA | H | $CH(CH_3)$* | 502 ($M^+$ + 1) |
|   |   |   |   | 520 ($M^+$ + 18) |
| 10 | 3,5-(diCl)—Ph—$SO_2$ | n-butyl | — | 472 ($M^+$ + 1) |
|   |   |   |   | 492 ($M^+$ + 18) |
| 11 | 3,5-(diCl)—Ph—$SO_2$ | benzyl | — | 506/508 ($M^+$ + 1) |
|   |   |   |   | 524 ($M^+$ + 18) |
| 12 | 3,5-(diCl)—Ph—$SO_2$ | phenyl* | — | 492 ($M^+$) |
| 13 | 3,5-(diCl)—Ph—$SO_2$ | 4-biphenylmethyl | — | 582 ($M^+$) |
| 14 | 3,5-(diCl)—Ph—$SO_2$ | phenyl* | $CH_2$ | 520 ($M^+$) |
| 15 | 3,5-(diCl)—Ph—$SO_2$ | benzyl* | $CH_2$ | 521 ($M^+$ + 1) |
|   |   |   |   | 538 ($M^+$ + 18) |
| 16 | 3,5-(diCl)—Ph—$SO_2$ | isobuty*l | $CH_2$ | 487 ($M^+$ + 1) |
| 17 | 3,5-(diCl)—Ph—$SO_2$ | benzyl# | — | 507 ($M^+$ + 1) |
| 18 | benzoyl | 4-biphenylmethyl | — | 496 ($M^+$ + 18) |
| 19 | phenylacetyl | 4-biphenylmethyl | — | 510 ($M^+$ + 18) |
| 20 | 3,5-(diCl)-benzoyl | 4-biphenylmethyl | — | 564 ($M^+$ + 18) |
| 21 | n-Bu—$SO_2$ | 4-biphenylmethyl | — | 495 ($M^+$ + 1) |
| 22 | 3-(CN)—Ph—$SO_2$ | 4-biphenylmethyl | — | 540 ($M^+$ + 1) |
| 23 | 3-(F)—Ph—$SO_2$ | 4-biphenylmethyl | — | 533 ($M^+$ + 1) |
| 24 | 4-(OMe)—Ph—$SO_2$ | 4-biphenylmethyl | — | 544 ($M^+$) |
| 25 | 3-(CF$_3$)—Ph—$SO_2$ | 4-biphenylmethyl | — | 583 ($M^+$ + 1) |
| 26 | 3-(Cl)—Ph—$SO_2$ | 4-biphenylmethyl | — | 550 ($M^+$ + 1) |
| 27 | Ph—$SO_2$ | 4-biphenylmethyl | — | 515 ($M^+$ + 1) |
| 28 | 4-(F)—Ph—$SO_2$ | 4-biphenylmethyl | — | 533 ($M^+$ + 1) |
| 29 | 3-(Me)—Ph—$SO_2$ | 4-biphenylmethyl | — | 546 ($M^+$ + 18) |
| 30 | 3,4-(diCF$_3$)—Ph—$SO_2$ | 4-biphenylmethyl | — | 651 ($M^+$ + 1) |
| 31 | 4-(OCF$_3$)—Ph—$SO_2$ | 4-biphenylmethyl | — | 599 ($M^+$ + 1) |
| 32 | 1-Me-4 imidazolyl-$SO_2$ | 4-biphenylmethyl | — | 519 ($M^+$ + 1) |
| 33 | 4-(Cl)—Ph—$SO_2$ | 4-biphenylmethyl | — | 550 ($M^+$ + 1) |
| 34 | 3,4-(diCl)—Ph—$SO_2$ | 4-biphenylmethyl | — | 583, 585 ($M^+$) and ($M^+$ + 2) |
| 35 | 2,3,4-(triF)-Ph—$SO_2$ | 4-biphenylmethyl | — | 569 ($M^+$ + 1) |
| 36 | 2-(Cl)—Ph—$SO_2$ | 4-biphenylmethyl | — | 549, 566 ($M^+$) and ($M^+$ + 17) |
| 37 | 3-(Cl)-4-(F)—Ph—$SO_2$ | 4-biphenylmethyl | — | 567 ($M^+$ + 1) |
| 38 | 2-thienyl-$SO_2$ | 4-biphenylmethyl | — | 521 ($M^+$ + 1) |

-continued

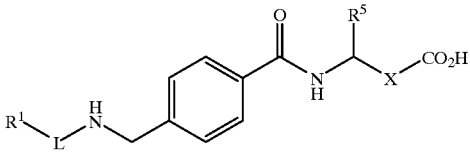

| Ex | R¹—L | R⁵ | X | Observed FAB MS |
|---|---|---|---|---|
| 39 | 2-(COOH)—Ph—SO₂ | 4-biphenylmethyl | — | 559 (M⁺ + 1) |
| 40 | 5-(Cl)-2-thienyl-SO₂ | 4-biphenylmethyl | — | 555 (M⁺ + 1) |
| 41 | 3,5-(diCl)—Ph—CO— | 4-biphenylmethyl | — | 564 (M⁺ + 18) |

EXAMPLE 42

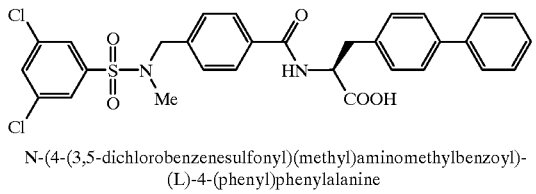

N-(4-(3,5-dichlorobenzenesulfonyl)(methyl)aminomethylbenzoyl)-(L)-4-(phenyl)phenylalanine Sulfonamide of Example 13 was alkylated in accordance with the procedure described in Step G of the General Procedure above to provide the title compound. 300 MHz $^1$H NMR (CD$_3$OD): 3.16 and 3.40 (AB dd, 2H); 4.25 (3H, s); 4.91 (m, 1H); 7.25–7.80 (m, 16H). FABMS: Calc. C$_{30}$H$_{26}$N$_2$O$_5$SCl$_2$: 597; Obs.: 598.

EXAMPLE 43

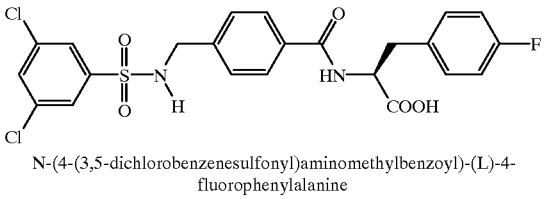

N-(4-(3,5-dichlorobenzenesulfonyl)aminomethylbenzoyl)-(L)-4-fluorophenylalanine

Step A. Preparation of N-[4-(N-Fmoc-aminomethyl)benzoyl]-(L)-4-fluorophenylalanine, t-butyl ester 0.3 g (0.8 mmol) of N-FMOC-4-aminomethylbenzoic acid (see general method above), 0.19 g (0.80 mmol) L-4-fluorophenylalanine-t-butyl ester, 0.40 g (1.20 mmol) HBTU and 0.16 g (1.20 mmol) of N-hydroxybenzotriazole hydrate were combined in 10 ml of dry DMF. The mixture was treated with 0.52 g (4.02 mmol) of diisopropylethylamine. The reaction mixture was stirred for 1 hours, diluted with 50 ml of EtOAc and washed with 1N HCl (2×15 ml), saturated sodium bicarbonate solution (2×15 ml) and brine (1×15 ml). The organic phase was dried over MgSO$_4$, filtered and concentrated in vacuo. $^1$H-NMR (CDCl$_3$, 400 MHz):1.45 (s, 9H); 3.21 9t, 2H); 4.21 (t, 1H); 4.41 (d, 1H); 4.50 (d, 1H); 4.91 (q, 1H); 6.75 (d, 1H); 6.97 (t, 2H); 7.13 9m, 2H); 7.30 (t, 4H); 7.39 (t, 2H); 7.59 (d, 2H); 7.70 (d, 2H); 7.78 (d, 2H).

Step B. Preparation of N-[4-(aminomethyl)benzoyl]-(L)-4-fluorophenyl, t-butyl ester The product of Step A was dissolved in 8 ml of CH$_2$Cl$_2$ and 2 ml of piperidine for 1 hour. The reaction mixture was diluted with EtOAc and washed with water, saturated sodium bicarbonate and brine. The reaction mixture was dried over MgSO$_4$, filtered and concentrated in vacuo to give the desired product. $^1$H-NMR (CD$_3$OD, 400 MHz):3.07 (ABq, 1H); 3.21 (ABq, 1H); 3.83 (s, 2H); 4.05 (t, 1H); 4.70 (t, 1H); 7.0 (t, 2H); 7.28 (m, 4H); 7.33 (t, 2H); 7.42 (d, 2H); 7.68 (d, 2H); 7.72 (d, 2H); 7.75 (d,2H).

Step C. Preparation of t-butyl ester of the Title Compound

To a solution of 0.025 g (0.067 mmol) of the product of Step B in 3 ml of CH$_2$Cl$_2$ and 0.024 ml (0.134 mmol) of diisopropylethylamine was added 16.45 mg of 3,5-dichlorophenylsulfonyl chloride. The reaction mixture was stirred at room temperature for 3 hours. The solution was concentrated in vacuo and the residue was purified by preparatory thin layer chromatography over silica gel eluting with 40% EtOAc/hexanes to give the product as a foam. $^1$H-NMR (CDCl$_3$, 400 MHz):1.42 (s, 9H); 3.19 (m, 2H); 4.22 (d, 2H); 4.88 (q, 1H); 4.97 (t, 1H); 6.60 (d, 1H); 6.95 (t, 2H); 7.12 (dd, 2H); 7.26 (d, 2H); 7.51 (d, 1H); 7.63–7.66 (m, 4H).

Step D Preparation of the Title Compound

The product of Step C was stirrred in 2 ml of 50% TFA/CH$_2$Cl$_2$ for 3 hours. The solution was concentrated in vacuo to give the desired product as a glass. $^1$H-NMR (CD$_3$OD, 400 MHz):3.1 (ABq, 1H); 3.31 (ABq, 1H); 4.20 (s, 2H); 4.82 (m, 1H); 6.98 (t, 2H); 7.26 (m, 4H); 7.56–7.65 (m, 4H); 8.41 (bd, 1H). FABms obsrved:525 (M⁺+1).

EXAMPLE 44

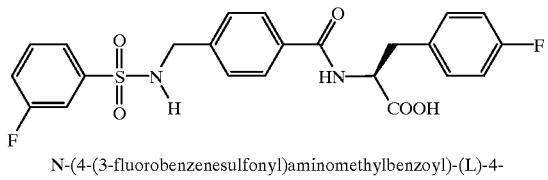

N-(4-(3-fluorobenzenesulfonyl)aminomethylbenzoyl)-(L)-4-fluorophenylalanine

The title compound was prepared following the procedure described in Example 43. During Step C two products were formed and were separated by preparatory thin layer chromatography eluting with 40% EtOAc/hexanes. The less polar product was the bis-sulfonamide and was discarded. The more polar product was the desired intermediate and was deprotected as described in Step 4. $^1$H-NMR (CD$_3$OD, 400 MHz):3.09 and 3.31 (ABdd, 2H); 4.12 (s, 2H); 4.81 (dd, 1H); 6.98 (t, 2H); 7.25–7.31 (m, 5H); 7.51 (m, 2H); 7.62 (m, 3H). FABms: observed 475 (M⁺+1).

EXAMPLE 45

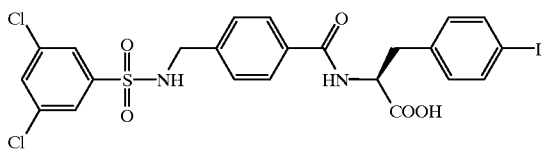

N-(4-(3,5-dichlorobenzenesulfonyl)aminomethylbenzoyl)-(L)-4-iodophenylalanine

Step A. Preparation of the t-butyl ester of the Title Compound

L-4-iodophenylalanine t-butyl ester was commited to the same sequence as described in Example 43. In Step B diethylamine was used in place of piperidine for removal of the FMOC group. The product was purified by Biotage flash chromatography over silica gel eluting with 10% MeOH/ $CH_2Cl_2$ followed by 1% $NH_4OH$, 14% MeOH 85% $CH_2Cl_2$ to give the intermediate amine. The amine (0.1 g (0.21 mmol) was sulfonylated by 3,5-dichlorosulfonylchloride (56.7 mg (0.23 mmol) in 5 ml of $CH_2Cl_2$ in the presence of 33.2 mg (0.42 mmol) of pyridine. After 4 hours the reaction mixture was diluted with EtOAc and washed with 1N HCl, saturated sodium bicarbonate solution and brine. The organic phase was dried over $MgSO_4$, filtered and concentrated in vacuo. The residue was purified by preparatory flash chromatography eluting with 30% EtOAc/hexanes to give the desired product. $^1$H-NMR ($CDCl_3$, 400 MHz):1.42 (s, 9H); 3.15 (m, 2H); 4.22 (d, 2H); 4.89 (q, 1H); 5.09 (bt, 1H); 6.60 (d, 1H); 6.89 (d, 2H); 7.25 (d, 2H); 7.50 (m, 1H); 7.58 (d, 2H); 7.61–7.65 (m, 4H).

Step B. Preparation of the Title Compound

The product of Step A was stirred in 50% $TFA/CH_2Cl_2$ for 3 hours and concentrated in vacuo to give the desired product. $^1$H-NMR ($CD_3OD$, 400 MHz): 3.05 (dd, 2H); 4.20 (s, 2H); 4.85 (dd, 1H); 7.05 (d, 2H); 7.25 (d, 2H); 7.55–7.65 (m, 7H).

EXAMPLE 46

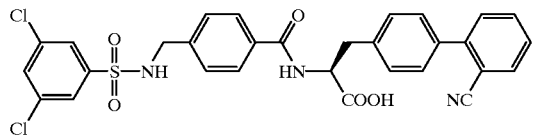

N-(4-(3,5-dichlorobenzenesulfonyl)aminomethylbenzoyl)-(L)-4-(2'-cyanophenyl)phenylalanine Step A. Preparation of N-(4-(3,5-dichlorobenzenesulfonyl)-aminomethylbenzoyl)-(L)-4-trimethylstannyl)phenylalanine The product of Step A of Example 45 (0.2 g (0.3 mmol) was combined in 4 ml of dioxane with 0.135 g (0.4 mmol) of hexamethylditin, 13.9 mg (0.33 mmol) of lithium chloride, 1.6 mg (0.006 mmol) of triphenylphosphine and 26.3 mg (0.015 mmol) of tetrakistriphenylphosphine. The mixture was heated to 80° C. for 60 minutes at which time the reaction mixture turned black. The mixture was diluted with EtOAc and was washed with water and brine and was dried over $MgSO_4$. The mixture was filtered and the solution was concentrated in vacuo. The residue was purified by preparatory thin layer chromatography eluting with 30% EtOAc/hexanes to give the desired stannane. $^1$H-NMR ($CDCl_3$, 400 MHz): 0.24 (s, 9H); 1.42 (s, 9H); 3.19 (m, 2H); 4.18 (d, 2H); 4.91 (q, 1H); 5.49 (bq, 1H); 6.59 (d, 1H); 7.12 (d, 2H); 7.19 (d, 2H); 7.38 (d, 2H); 7.49 (m, 1H); 7.56 (d, 2H); 7.69 (d, 2H).

Step B. Preparation of the t-butyl ester of the Title Compound

To a solution of 50 mg (0.0725 mmol) of the product of Step A in 1.5 ml of toluene was added 33.2 mg (0.145 mmol) of 2-iodobenzonitrile and 10 mg of bistriphenylphosphine palladium dichloride. The solution was heated to 100° C. overnight. The reaction mixture was diluted with EtOAc and washed with water, saturated sodium bicarbonate solution and brine. The organic phase was dried over $MgSO_4$, filtered and concentrated in vacuo. The residue was purified by preparatory thin layer chromatography eluting with 35% EtOAc/hexanes to provide the product. $^1$H-NMR ($CD_3OD$, 400 MHz): 1.45 (s, 9H); 3.15–3.35 (m, 2H); 4.2 (s, 2H); 4.81 (m, 1H);7.26 (d, 2H); 7.40–7.85 (m, 13H).

Step C. Preparation of the Title Compound

The product of Step B was stirred with 50% $TFA/CH_2Cl_2$ for 2 hours. Concentrated in vacuo to give the desired product. $^1$H-NMR ($CD_3OD$, 400 MHz): 3.22 (m, 1H); 3.45 (m, 1H); 4.19 (s, 2H); 7.25 (d, 2H); 7.42 (d, 2H); 7.50–7.69 (m, 7H); 7.62 (d, 2H); 7.70 (t, 1H); 7.80 (d, 1H). FABms: Calc:607; Obs:608 ($M^++1$) and 625 ($M^++18$).

EXAMPLE 47

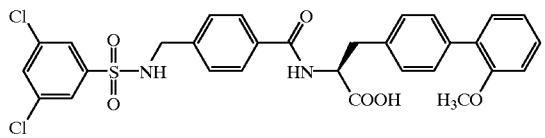

N-(4-(3,5-dichlorobenzenesulfonyl)aminomethylbenzoyl)-(L)-4-(2'-methoxyphenyl)phenylalanine Step A. Preparation of the t-butyl ester of the Title Compound A solution of 50 mg (0.08 mmol) of the product of Step A Example 45, 13.4 mg (0.09 mmol) of 2-methoxybenzeneboronic acid and 10 mg of tetrakistriphenylphosphine palladium in 3 ml of 3:1 toluene/EtOH was treated with 0.09 ml (0.17 mmol) of 2N $Na_2CO_3$ in water. The reaction mixture was degassed and heated at 80° C. for 4 hours. The reaction mixture was diluted with EtOAc and washed with water, saturated sodium bicarbonate solution and brine. The organic phase was dried over $MgSO_4$, filtered and concentrated in vacuo. The residue was purified by preparatory thin layer chromatography eluting with 35% EtOAc/hexanes to provide the product. $^1$H-NMR ($CD_3OD$, 400 MHz): 1.43 (s, 9H); 3.15 and 3.24 (ABdd, 2H); 3.75 (s, 3H); 4.20 (s, 2H); 4.75 (dd, 1H); 6.98 9t, 1H); 7.02 (d, 1H); 7.21–7.31 (m, 6H); 7.40 (d, 2H); 7.52 (m, 1H); 7.59 (s, 2H); 7.68 (d, 2H).

Step B. Preparation of the Title Compound

The product of Step A was stirred for 2 hours with 50% $TFA/CH_2Cl_2$ and concentrated in vacuo to give the desired product. $^1$H-NMR ($CD_3OD$, 400 MHz): 3.15 and 3.37 (ABdd, 2H); 3.72 (s, 3H); 4.19 (s, 2H); 6.98 (t, 1H); 7.02 (d, 1H); 7.25 (m, 4H); 7.29 (bd, 2H); 7.41 (d, 2H); 7.50 (m, 1H); 7.58 (s, 1H); 7.65 (d, 2H). FABms: Calc:607; Obs:608 ($M^++1$) and 625 ($M^++18$). ). FABms: Calc:612; Obs: 630 ($M^++18$).

EXAMPLES 48–58

The following compounds are prepared following the procedure described in Example 47 using the appropriate boronic acid:

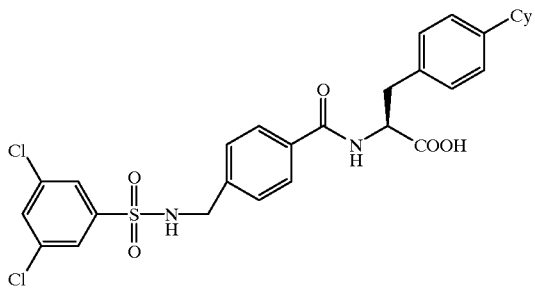

| Ex. | Cy | NMR/ HPLC | Observed FAB ms |
|---|---|---|---|
| 48 | 4-t-butylphenyl | Pure | 656 (M+ + 18) |
| 49 | 3-methoxyphenyl | Pure | 630 (M+ + 18) |
| 50 | 4-methoxyphenyl | Pure | 613 (M+ + 1) |
| 51 | 4-(methylthio)phenyl | Pure | — |
| 52 | 2-formylphenyl | Pure | 628 (M+ + 18) |
| 53 | 3-acetamidophenyl | Pure | 656 (M+ + 17) |
| 54 | 2-thienyl | Pure | — |
| 55 | 5-chloro-2-thienyl | Pure | 640 (M+ + 18) |
| 56 | 3-thienyl | Pure | — |
| 57 | 2-naphthyl | Pure | — |
| 58 | 2-cyanophenyl (D-enatiomer) | Pure | — |

EXAMPLE 59

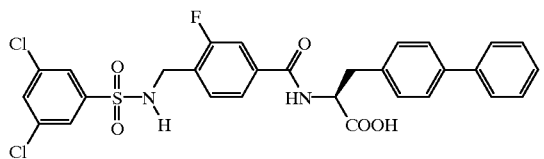

N-(4-(3,5-dichlorobenzenesulfonyl)aminomethyl-3-fluorobenzoyl)-(L)-4-(phenyl)phenylalanine Step A. Preparation of Methyl 4-(aminomethyl)-3-(fluoro)-benzoate To a solution of 2.47 g (0.01 mole) of methyl 4-(bromomethyl)-3-(fluoro)-benzoate in 10 ml of dimethylformamide was added 0.71 g (0.011 mole) of sodium azide. The reaction mixture was stirred over night at room temperature, diluted with water (50 ml) and extracted with ethyl acetate (3×20 ml). The combined organic extracts were dried over MgSO$_4$, filtered and concentrated in vacuo to give the intermediate azide. To a solution of the product in 10 ml of ethyl acetate was added 1 mole equivalent of acetic acid followed by 200 mg of 10% Pd/C. The mixture was hydrogenated over night at 50 psi at room temperature. The mixture was filtered and made basic by addition of 1N NaOH solution. The phases were separated and the organic phase was dried over Na$_2$SO$_4$, filtered and concentrated in vacuo to give the amine as an oil. 300 MHz $^1$H NMR (CDCl$_3$): 3.91 (s, 3H); 4.95 (s, 2H); 7.45 (m, 1H); 7.69 (d, 1H); 7.82 (d, 1H).

Step B. Preparation of Methyl 4-((N-3,5-dichlorphenylsulfonyl)aminomethyl)-3-(fluoro)-benzoate 0.38 g (2.1 mmol) of the product of Step A was dissolved in 5 ml of CH$_2$Cl$_2$ and treated with 0.33 g (4.1 mmol) pyridine at 0° C. To the solution was added 0.56 g (2.3 mmol) of 3,5-dichlorphenylsulfonyl chloride. The reaction mixture was allowed to warm to room temperature over night. Dilution with ethyl acetate gave a white precipitate which was recovered by filtration. Recovered 0.32 g. 300 MHz $^1$H NMR (CDCl$_3$):3.92 (s, 3H); 4.32 (d, 2H); 5.20 (t, 1H); 7.33 (t, 1H); 7.49 (m, 1H); 7.58–7.65 (m, 3H); 7.76 (d, 1H).

Step C. Preparation of 4-((N-3,5-dichlorophenylsulfonyl)aminomethyl)-3-(fluoro)-benzoic acid 0.32 g of the product of Step B was suspended in 5 ml of MeOH to which was added 2.4 ml of 1N NaOH solution. The reaction mixture was stirred over night at room temperature and was concentrated in vacuo remove methanol. The aqueous solution was acidified to give a white precipitate which was collected by filtration, washed with water and was dried in vacuo to give 0.28 g of the desired product. 300 MHz $^1$H NMR (CD$_3$OD): 4.29 (s, 3H); 7.35 (t, 1H); 7.50 (dd, 1H); 7.58 (m, 3H); 7.70 (dd, 1H).

Step D. Preparation of the Title Compound

To a solution of 87 mg (0.23 mmol) of the product of Step C in 1.5 ml of DMF was added 71 mg (0.21 mmol) of biphenylalanine t-butyl ester hydrochloride followed by 31 mg of N-hydroxybenzotriazole, 87 mg (0.23 mmol) of HBTU and 86 mg (0.67 mmol) of diisopropyl ethyl amine. The solution was stirred over night at room temperature, diluted with 20 ml of ethyl acetate and washed with 1N HCl (2×5 ml), saturated NaHCO$_3$ solution (2×5 ml) and brine (1×5 ml) and was dried over MgSO$_4$. The mixture was filtered and concentrated in vacuo and the residue was purified by preparatory thin layer chromatography over silica gel eluting with 25% EtOAc/hexanes. The product was dissolved in 5 ml of 50% TFA/CH$_2$Cl$_2$ and stirred for 90 minutes. The solution was concentrated in vacuo to give the desired product. 300 MHz $^1$H NMR (CD$_3$OD): 3.1 and 3.27 (ABdd, 2H); 4.10 (s, 2H); 4.86 (dd, 1H); 7.10–7.50 (m, 15H). FABMS: Calc. C$_{29}$H$_{33}$Cl$_2$F$_1$N$_2$O$_5$S$_1$; 601; Obs.: 618, 620.

EXAMPLE 60

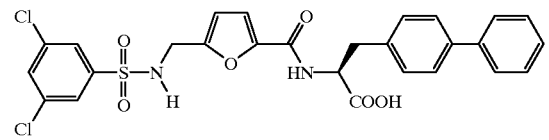

N-(5-(3,5-dichlorobenzenesulfonyl)aminomethyl-2-furroyl)-(L)-4-(phenyl)phenylalanine The procedure described in Example 59 was followed using ethyl (5-(chloromethyl)-2-furancarboxylate as the starting material. During Step B a mixture of the desired product and an unknown side product formed. The mixture was carried through the remainder of the synthesis and provided the desired product. 300 MHz 1H NMR (CD3OD): 3.13 and 3.35 (ABdd, 2H); 4.22 (s, 2H); 4.85 (m, 1H); 6.22 (d, 1H); 6.89 (d, 1H); 7.25–7.60 (m, 12H). FABMS: C27H33Cl2N2O6S 1: Calc.: 573; Obs.: 573, 590.

EXAMPLE 61

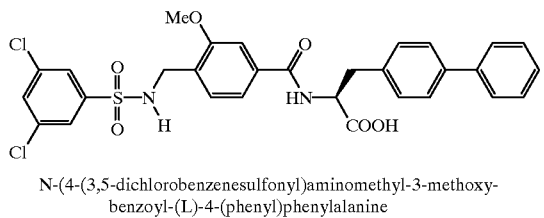

N-(4-(3,5-dichlorobenzenesulfonyl)aminomethyl-3-methoxy-
benzoyl-(L)-4-(phenyl)phenylalanine The procedure described in Example 59 was followed using methyl (4-(bromomethyl)-3-(methoxy)-benzoate as the starting material. The coupling with biphenyl alanine was carried out on Wang resin as described above to give the desired product. 300 MHz $^1$H NMR (CD$_3$OD): 3.15 and 3.38 (ABdd, 2H); 3.72 (s, 3H); 4.19 (s, 2H); 4.89 (m, 1H); 7.15–7.50 (m, 13H); 7.70 (d, 2H). FABMS: C$_{27}$H$_{33}$Cl$_2$N$_2$O$_6$S$_1$: Calc.: 573; Obs.: 573, 590.

EXAMPLE 62

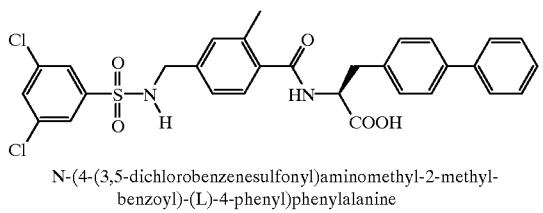

N-(4-(3,5-dichlorobenzenesulfonyl)aminomethyl-2-methyl-
benzoyl)-(L)-4-phenyl)phenylalanine Step A. Preparation of ethyl-4-(bromomethyl)-2-(methyl)-benzoate The method described in J. Med Chem. 583 1981 was utilized. 1.5 g (9 mmol) of ethyl-2,4-dimethylbenzoate was heated in 15 ml of carbon tetrachloride in the presence of 1.65 g (9.3 mmol) of N-bromosuccinimide and a catalytic amount of benzoyl peroxide. After 2 hours the reaction mixture was cooled to room temperature, filtered and concentrated in vacuo. The residue was purified by MPLC on a Lobar C column eluting with 1.5% EtOAc/hexanes. 0.74 g of a 1:1 mixture of regioisomeric bromides was recovered. The mixture was heated at 140° C. for 90 minutes and cooled to provide a solid. The residue was broken up and stirred with hexanes and gently heated. The mixture was cooled to room temperature and the precipitated lactone removed by filtration. The filtrate was concentrated in vacuo to give 0.34 g of the desired bromide. 300 MHz $^1$H NMR (CDCl$_3$):1.38 (t, 3H); 2.59 (s, 3H); 4.33 (q, 2H); 4.41 (s, 2H); 7.22 (m, H); 7.89 (d, 1H).

Step B. Preparation of the Title Compound

The bromide from Step A was converted to the desired product using the procedures described in Example 59. 300 MHz $^1$H NMR (CD$_3$OD):2.12 (s, 3H); 3.15 and 3.42 (ABdd, 2H); 4.11 (s, 2H); 4.85 (m, 1H (buried)); 6.95 (s, 1H); 7.00 (d, 1H); 7.12 (d, 1H).7.30–7.68 (m, 12H). FABMS: C$_{30}$H$_{36}$Cl$_2$N$_2$O$_6$S$_1$: Calc.: 596; Obs.: 597.

EXAMPLE 63

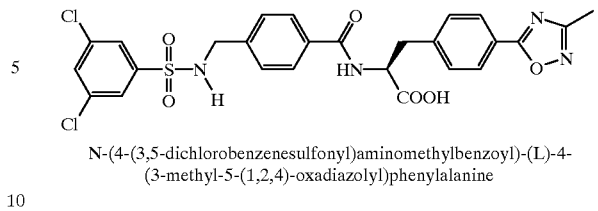

N-(4-(3,5-dichlorobenzenesulfonyl)aminomethylbenzoyl)-(L)-4-
(3-methyl-5-(1,2,4)-oxadiazolyl)phenylalanine Step A: Preparatioin of N-Boc-L-4-(3-methyl-1,2,4-oxadiazol-5-yl)-phenylalanine, t-butyl ester To a solution of 0.32 g (0.71 mmol) of N-Boc-(L)-4-iodophenylalanine t-butyl ester in 3.0 ml of toluene contained in a 5 ml round bottom flash fitted with a condenser topped with a T-valve (one side of which is connected to a balloon of carbon monoxide the other side to a vacuum source) was added 0.15 g (2.1 mmol) of methyl amide oxime, 25 mg of bistriphenylphosphine palladium dichloride and 0.14 g (1.4 mmol) of triethylamine. The vessel was evacuated and flushed with CO gas three times and then heated at 90° C. under CO overnight. The reaction mixture was diluted with 25 ml of ethyl acetate and washed with water (2×25 ml) and brine (1×25 ml). The mixture was filtered and concentrated in vacuo. The residue was purified by Biotage flash chromatography eluted with 15% ethyl acetate/hexanes to give 0.18 g of the desired product (63% yield). 300 MHz $^1$H NMR (CDCl$_3$): δ1.40 (s, 18H); 2.42 (s, 3H); 3.10 (m, 2H); 4.45 (dd, 1H); 5.09 (d, 1H); 7.31 (d, 2H); 8.0 (d, 2H).

Step B. Preparation of 4-[N-(3,5-dichlorphenylsulfonyl) aminomethyl]-benzoic acid 0.3 g (1.98 mmol) of 4-aminomethylbenzoic acid was dissolved in 4.1 ml of 1N NaOH solution and 4 ml of dioxane. To this mixture was added a solution of 3,5-dichlorphenyl sulfonyl chloride in 4 ml of dioxane. The reaction mixture was stirred over night at room temperature, acidfied and filtered to give 0.42 g of the desired acid. 300 MHz $^1$H NMR (DMSOd6): 4.20 (d, 2H); 7.31 (d, 2H); 7.65 (s, 2H); 7.82 (d, 2H); 7.89 (s, 1H); 8.55 (t, 1H).

Step C. Preparation of the Title Compound

N-Boc-L-4-(3-methyl-1,2,4-oxadiazol-5-yl)-phenylalanine t-butyl ester (0.18 g, 0.46 mmol) was stirred overnight with 5 equivalents of 1.5M HCl/ethyl acetate solution. The resulting white precipitate was filtered and dried in vacuo to give 0.12 g (0.35 mmol) of the amine hydrochloride. 0.03 g (0.088 mmol) of the amine hydrochloride was suspended in 1 ml of DMF and stirred overnight at room temperature in the presence of 47 mg (0.13 mmol) of 4-(N-3,5-dichlorophenylsulfonylaminomethyl)-benzoic acid, 49 mg (0.13 mmol) of HBTU 17.5 mg of HOBt and 33 mg of diisopropylethyl amine. Following aqueous work up the product was purified by Biotage chromatography over silica gel eluting with 30% EtOAc/hexanes to give the desired product. The material was dissolved in 2 ml of 50% TFA/CH$_2$Cl$_2$ for two hours and then concentrated in vacuo and azeotroped from toluene to give the desired product. FABMS: Calc. C$_{25}$H$_{32}$Cl$_2$N$_4$O$_6$S$_1$: 588; Obs.: 589

EXAMPLE 64

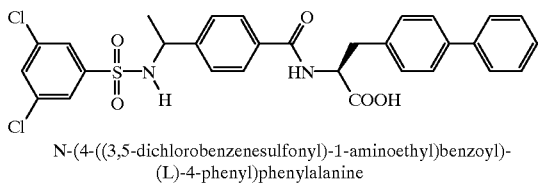

N-(4-((3,5-dichlorobenzenesulfonyl)-1-aminoethyl)benzoyl)-
(L)-4-phenyl)phenylalanine Step A. Preparation of methyl R,S-4-(1-bromoethyl)-benzoate 2.5 g (10 mmol) of 4-(1-bromoethyl)-benzoic acid was dissolved in 100 ml of methanol and treated with 1 ml of concentrated sulfuric acid. The solution was stirred for 18 hours, concentrated in vacuo and the residue was dissolved in 100 ml of EtOAc. The solution was washed with saturated sodium bicarbonate solution (3×25 ml) and was dried over $MgSO_4$, filtered and was concentrated in vacuo to give 1.5 g of an oil. 300 MHz $^1$H NMR ($CDCl_3$): 2.05 (d, 3H); 3.91 (s, 3H); 5.20 (q, 1H); 7.50 (d, 2H); 8.00 (d, 2H).

Step B. Preparation of R,S-4-(1-((N-3,5-dichlorophenylsulfonyl)amino)ethyl)-benzoic acid The product of Step A was committed to the sequence described in Example 59 Steps A–C to give the desired product. 300 MHz $^1$H NMR ($CDCl_3$):1.39 (d, 3H); 4.45 (q, 1H); 7.08 (d, 2H); 7.29 (s, 1H); 7.31 (s, 2H); 7.77 (d, 2H).

Step C. Preparation of the Title Compound

The product of Step B was coupled to L-biphenylalanine Wang resin in the usual manner, washed and cleaved to give the desired product. 300 MHz $^1$H NMR ($CD_3OD$): 1.42 (d, 3H); 3.18 and 4.40 (ABdd, 2H); 4.51 (q, 1H); 5.11 (buried, 1H); 7.10 (d, 2H); 7.22–7.60 (m, 14H). FABMS: Calc. $C_{30}H_{26}N_2O_5S_1Cl_2$; 597; Obs.: 615.

EXAMPLE 65

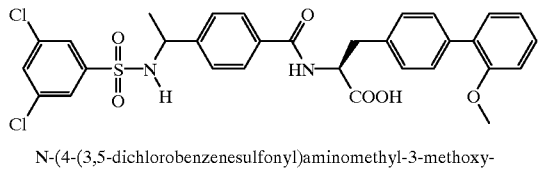

N-(4-(3,5-dichlorobenzenesulfonyl)aminomethyl-3-methoxy-
benzoyl)-(L)-4-phenyl)phenylalanine The product of Example 64 Step B was coupled with 2'-methoxy-biphenylalanine t-butyl ester hydrochloride as in Example 59 Step D. The product, following purification by preparatory thin layer chromatography eluting 30% EtOAc/hexanes was treated with 50% $TFA/CH_2Cl_2$ for 2 hours and was concentrated in vacuo to give the desired product as a glass. 300 MHz $^1$H NMR ($CD_3OD$):

EXAMPLE 66

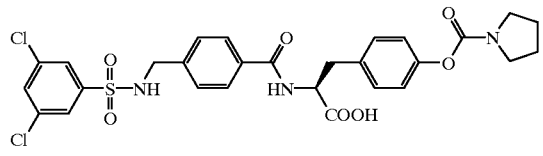

N-(4-(3,5-dichlorobenzenesulfonyl)aminomethylbenzoyl)-(L)-O-
(1-pyrrolidinyl-carbonyl)tyrosine Step A. Preparation of 4-(N-CBz-aminomethyl)-benzoic acid 10.0 g (66 mmol) of 4-aminomethylbenzoic acid was dissolved in 33 ml of 2N NaOH solution (66 mmol) and 30 ml of THF. 12.45 g (73 mmol) of benzyl chloroformate and 37.5 ml of 2N NaOH solution was added in aliquots at 0° C. over 20 minutes. The reaction was stirred at room temperature over night and concentrated in vacuo to remove THF. 2N HCl was added to acidify to pH2–3. The precipitated solid was recovered by filtration and washed with ether to remove excess benzyl chloroformate. The solid was dried in vacuo to give 18.8 g of the desired product. 400 MHz $^1$H NMR ($CD_3OD$): 4.31 (s, 2H); 5.09 (s, 2H); 7.30 (m, 7H); 7.91 (d, 2H).

Step B. Preparation of O-t-butyl-N-[4-(N-Cbz-aminomethyl)benzoyl]-(L)-tyrosine, methyl ester 5.0 g (17.5 mmol) of the product of Step A was combined in 60 ml of DMF with 5.05 g (17.5 mmol) of L-4-t-butoxy-phenylalanine methyl ester hydrochloride, 4.73 g (35 mmol) of HOBt, 13.3 g (35 mmol) HBTU and 12.2 ml of diisopropylethylamine. After 2 hours the reaction mixture was diluted with 150 ml of EtOAc and was washed with 2×50 ml of 1N HCl, 2×50 ml saturated $NaHCO_3$ and 1×50 ml brine. The solution was dried over $MgSO_4$, filtered and concentrated in vacuo and the residue was purified by flash chromatography (Biotage) over silica gel eluting with 20% EtOAc/hexanes to give 6.53 g of the desired product. 400 MHz $^1$H NMR ($CDCl_3$): 1.32 (s, 9H); 3.20 (t, 2H); 3.73 (s, 3H); 4.42 (d, 2H); 5.13 (s, 2H); 6.51 (d, 1H); 6.91 (d, 2H); 7.02 (d, 2H); 7.30–7.40 (m, 7H); 7.67 (d, 2H).

Step C. Preparation of N-[4-(N-Cbz-aminomethyl)benzoyl]-(L)-tyrosine, methyl ester 5.5 g of the product of Step B was stirred with 50 ml of 50% $TFA/CH_2Cl_2$ for 90 minutes. The reaction mixture was concentrated in vacuo and azeotroped with toluene to give a white solid. 4.75 g was recovered. 400 MHz $^1$H NMR ($CDCl_3$): 3.10 and 3.20 (ABdd, 2H); 3.76 (s, 3H); 4.38 (d, 2H); 5.01 (m, 1H); 5.12 (s, 2H); 6.67 (d, 1H); 6.70 (d, 2H); 6.92 (d, 2H); 7.12–7.38 (m, 7H); 7.61 (d, 2H).

Step D. Preparation of O-(1-pyrrolidinylcarbonyl)-N-[4-(N-Cbz-aminomethyl)benzoyl]-(L)-tyrosine, methyl ester 1.3 ml of a 1M solution of sodium hexamethyldisilazide in THF was added to a solution of 0.5 g of the product of Step A in 8 ml of THF at 0° C. The reaction mixture was stirred at 0° C. for 1 hour. 120 mg (2.2 mmol) of pyrolidine carbonyl chloride was added in 2 ml of THF. The reaction mixture was stirred at 0° C. for 30 minutes and then at room temperature for 90 minutes. The reaction mixture was diluted with ethyl acetate and washed with saturated sodium bicaronate solution and brine and was dried over MgSO4. The mixture was filtered and concentrated in vacuo and the residue was purified by flash chromatography (Biotage) over silica gel eluting with 25% $EtOAc/CH_2Cl_2$ to give 465 mg of a foam. 400 MHz $^1$H NMR ($CDCl_3$): 1.92 (m, 4H); 3.22 (m, 2H); 3.42 (t, 2H); 3.52 (t, 2H); 3.72 (s, 3H); 4.39 (d, 2H); 5.05 (m, 1H); 5.11 (s, 2H); 6.11 (t, 1H); 7.05 (m, 4H); 7.26–7.40 (m, 7H); 7.63 9d, 2H).

Step E. Preparation of O-(1-pyrrolidinylcarbonyl)-N-[4-(aminomethyl)benzoyl]-(L)-tyrosine, methyl ester 73.3 mg of the product of Step D was dissolved in 5 ml of methanol and hydrogenated at atmospheric pressure for 2 hours over 10 mg of 10% Pd/C. The mixture was filtered and the filtrate was concentrated in vacuo to give 50 mg of the desired product. 300 MHz $^1$H NMR ($CD_3OD$): 1.95 (m, 4H); 3.12 and 3.32 (ABdd, 2H); 3.35 (s, 2H); 3.39 (t, 2H); 3.65 (t, 2H); 3.72 (s, 2H); 5.86 (m, burried), 1H); 7.02 (d, 2H); 7.26 (d, 2H); 7.51 9d, 2H); 7.82 (d, 2H).

Step F. Preparation of methyl ester of the Title Compound 49 mg (0.116 mmol) of the product of Step E in solution in 1 ml of dry DMF was treated with 45 mg (0.35 mmol)

DIEA followed by 28.4 mg (0.116 mmol) of 3,5-dichlorophenylsulfonyl chloride. After 30 minutes the reaction mixture was diluted with ethyl acetate and washed with saturated sodium bicarbonate solution and brine and was dried over $MgSO_4$. The mixture was filtered and concentrated in vacuo and the residue was purified by preparatory thin layer chromatography eluting with 30% $EtOAc/CH_2Cl_2$ to give 48 mg of the desired product.

Step G. Preparation of the Title Compound 49 mg (0.074 mmol) of the product of Step F was dissolved in a mixture of 1 ml THF and 1 ml of MeOH. To the solution was added 0.41 ml of 1N NaOH solution. The solution was stirred at room temperature for 2 hours, concentrated in vacuo and the residue redissolved in water. The solution was acidified with 5% citric acid solution and the product was isolated by extraction with ethyl acetate. The combined organic extracts were dried over $MgSO_4$, filtered and concentrated in vacuo to give the desired product. 300 MHz $^1$H NMR ($CD_3OD$): 1.95 (m, 4H); 3.13 AND 3.30 (ABdd, 2H); 3.40 (t, 2H); 3.53 (t, 2H); 4.18 (s, 2H); 7.01 (d, 2H); 7.25 (d, 3H); 7.60–7.65 (m, 3H); 7.78 (s, 2H). FABMS: Calc. $C_{28}H_{27}Cl_2N_3O_7S$; 620; Obs.: 620

EXAMPLE 67

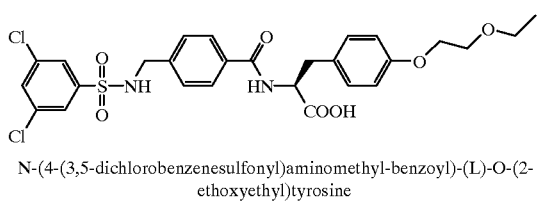

N-(4-(3,5-dichlorobenzenesulfonyl)aminomethyl-benzoyl)-(L)-O-(2-ethoxyethyl)tyrosine Step A. Preparation of O-[2-(ethoxy)ethyl]-N-[4-(N-Cbz-aminomethyl)benzoyl]-(L)-tyrosine, methyl ester 0.3 g (0.65 mmol) of the product of Example 66 Step C was dissolved in 10 ml of dry DMF and was treated with 0.5 g (3.24 mmol) of bromoethyl ethyl ether and 0.44 g (3.24 mmol) of potassium carbonate. The mixture was heated to 50° C. for 4 hours at which time a further 0.5 g of bromoethyl ethyl ether was added. The mixture was heated overnight at 50° C. The mixture was diluted with ethyl acetate and was washed with water, sodium bicarbonate solution and brine. The solution was dried over $MgSO_4$, filtered and concentrated in vacuo and the residue was purified by flash chromatography (Biotage) over silica gel eluting with 80% $CH_2Cl_2$/20% $CH_2Cl_2$ to give 260 mg of the desired product. 400 MHz $^1$H NMR ($CDCl_3$): 1.22 (t, 3H); 3.18 (m, 2H); 3.58 (q, 2H); 3.72 ((s, 3H); 3.76 (m, 2H); 4.07 (m, 2H); 4.40 (m, 2H); 5.02 (m, 1H); 5.12 (s, 2H); 6.50 (d, 1H); 6.22 (d, 2H); 6.99 (d, 2H); 7.30–7.38 (m, 7H); 7.67 (d, 2H).

Step B. Preparation of the Title Compound

The procedures outlined in Example 66 Steps E–G were applied to the product of Step A to give the desired product. 400 MHz $^1$H NMR ($CD_3OD$): 1.18 (t, 3H); 3.13 and 3.28 (ABdd, 2H); 3.56 (q, 2H); 3.72 (m, 2H); 4.06 (m, 2H); 4.20 (s, 2H); 4.80 (m, 1H); 6.86 (d, 2H); 7.18 (d, 2H); 7.25 (d, 2H); 7.55–7.62 (m, 5H) FABMS: Calc:$C_{27}H_{28}Cl_2N_3O_7S$; 595; Obs.: 612.

EXAMPLE 68

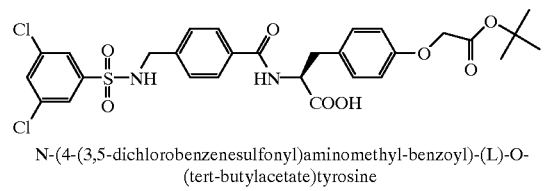

N-(4-(3,5-dichlorobenzenesulfonyl)aminomethyl-benzoyl)-(L)-O-(tert-butylacetate)tyrosine The procedure described in Example 66 was utilized, alkylating the tyrosine oxygen with t-butyl bromoacetate. The alkylation was complete within 4 hours. Purification of the alkylated product was carried out by Biotage flash chromatography over silica gel eluting with 15% EtOAc/$CH_2Cl_2$. The final product was isolated as described previously. 400 MHz $^1$H NMR ($CD_3OD$):1.45 (s, 9H); 3.06 and 3.23 (ABdd, 2H); 4.20 (s, 2H); 4.52 (s, 2H); 4.80 (m, 1H); 6.83 (m, 2H); 7.19 (t, 2H); 7.25 (m, 2H); 6.58–6.65 (m, 3H). FABMS: Calc:$C_{29}H30Cl_2N_2O_8S$; 637; Obs.: 654.

EXAMPLE 69

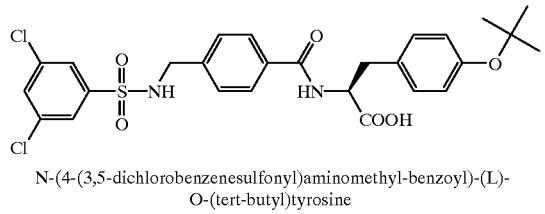

N-(4-(3,5-dichlorobenzenesulfonyl)aminomethyl-benzoyl)-(L)-O-(tert-butyl)tyrosine Commitment of the product of Step B of Example 66 to the sequence Step E–G of Example 66 provided the title compound. 400 MHz $^1$H NMR ($CD_3OD$):1.39 (s, 9H); 3.09 and 3.31 (buried) (ABdd, 2H); 4.20 (s, 2H); 4.90 (buried) (m, 1H); 6.91 (d, 2H); 7.19 (d, 2H); 7.25 (d, 2H); 6.58–6.63 (m, 4H); 8.32 (d, 1H). FABMS: Calc:$C_{27}H_{28}Cl_2N_2O_6S$; 579; Obs.: 596.

EXAMPLE 70

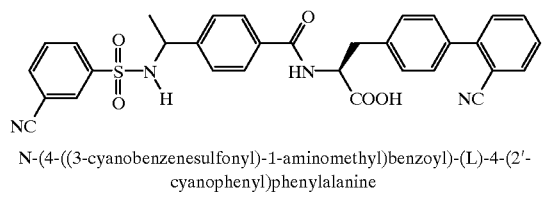

N-(4-((3-cyanobenzenesulfonyl)-1-aminomethyl)benzoyl)-(L)-4-(2'-cyanophenyl)phenylalanine The product of Example 64 Step B was commited to the methods described in the case of Example 59, sulfonylating with 3-cyanophenylsulfonyl chloride and the coupling the saponified product with 2'-cyano-biphenylalanine on Wang resin as in the general procedure to give the desired product. 400 MHz $^1$H NMR ($CD_3OD$): 1.33 (d, 3H); 3.25 and 3.40 (bs, 2H); 4.49 (q, 1H); 7.10 (d, 2H); 7.35–7.52 (m, 10H); 7.63 (m, 2H); 7.77 (d, 2H); 7.81 (d, 1H). FABMS. Calc. $C_{32}H_{36}N_4O_5S_1$; 578; Obs.: 579

EXAMPLE 71

Inhibition of VLA-4 Dependent Adhesion to BSA-CS-1 Conjugate

Step A. Preparation of CS-1 Coated Plates

Untreated 96 well polystyrene flat bottom plates were coated with bovine serum albumin (BSA; 20 μg/ml) for 2 hours at room temperature and washed twice with phosphate buffered saline (PBS). The albumin coating was next derivatized with 10 μg/ml 3-(2-pyridyldithio) propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-VaPro-Ser-Thr), which was synthesized by conventional solid phase chemistry and purified by reverse phase HPLC, was next added to the derivatized BSA at a concentration of 2.5 μg/ml and allowed to react for 2 hours at room temperature. The plates were washed twice with PBS and stored at 4° C.

Step B. Preparation of Fluorescently Labeled Jurkat Cells

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 μg/ml streptomycin and 2 mM Glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of $2 \times 10^6$ cells/ml in PBS containing a 1 μM concentration of a fluorogenic esterase substrate (2', 7'-bis-(2-carboxyethyl)-5-(and -6)carboxyfluorescein, acetoxymethyl ester; BCECF-AM; Molecular Probes Inc., Eugene, Oreg.; catalog #B-1150) for 30–60 minutes at 37° C. in a 5% $CO_2$/air incubator. The fluorescently labeled Jurkat cells were washed two times in PBS and resuspended in RPMI containing 0.25% BSA at a final concentration of $2.0 \times 10^6$ cells/ml.

Step C. Assay Procedure

Compounds of this invention were prepared in DMSO at 100× the desired final assay concentration. Final concentrations were selected from a range between 0.001 nM–100 μM. Three μL of diluted compound, or vehicle alone, were premixed with 300 μL of cell suspension in 96-well polystyrene plates with round bottom wells. 100 μL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 72

Antagonism of VLA-4 Dependent Binding to VCAM-Ig Fusion Protein

Step A: Preparation of VCAM-Ig

The signal peptide as well as domains 1 and 2 of human VCAM (GenBank Accession no. M30257) were amplified by PCR using the human VCAM cDNA (R & D Systems) as template and the following primer sequences: 3'-PCR primer:5'-AATTATAATTTGATCAACTTAC CTGTCAATTCTTTTACAGCCTGCC-3'; 5'-PCR primer: 5'-ATAGGAATTCCAGCTGCCACCATGCCTGGGAAG-ATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1: MPGKMVVILGASNILWIM-FAASQAFKIETTPESRYLAQIGDSVSLTC STTGCESPFFSWRTQIDSPLNGKVT-NEGTTSTLTMNPVSFGNEHSYLC TATCESRKLE-KGIQVEIYSFPKDPEIHLSGPLEAGKPITVKCSVADVY PFDRLEIDLLKGDHLMKSQE-FLEDADRKSLETKSLEVTFTPVIEDIGKV LVCRAKL-HIDEMDSVPTVRQAVKEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 μg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B: Preparation of $^{125}$I-VCAM-Ig

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C: VCAM-Ig Binding Assay

Compounds of this invention were prepared in DMSO at 100× the desired final assay concentration. Final concentrations were selected from a range between 0.001 nM-100 μM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Mass.) by making the following additions to duplicate wells: (i) 200 μL of binding buffer containing 1 mM $MnCl_2$; (ii) 20 μL of $^{125}$I-VCAM-Ig in binding buffer containing 1 mM $MnCl_2$ (final assay concentration~100 pM); (iii) 2.5 μL of compound solution or DMSO; (iv) and 0.5×10$^6$ cells in a volume of 30 μL. The plates were incubated at room temperature for 30 minutes, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 73
Antagonism of $\alpha_4\beta_7$ Dependent Binding to VCAM-Ig Fusion Protein
Step A: $\alpha_4\beta_7$ Cell line
RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/100 μg streptomycin/2 mM L-glutamine at 37° C., 5% carbon dioxide. The cells were pelleted at 1000 rpm for 5 minutes and then washed twice and resuspended in binding buffer (25 mM HEPES, 150 mM NaCl, 0.1% BSA, 3 mM KCl, 2 mM Glucose, pH 7.4).
Step B: VCAM-Ig Binding Assay
Compounds of this invention were prepared in DMSO at 100× the desired final assay concentration. Final concentrations were selected from a range between 0.001 nM–100 μM. Compounds were assayed in Millipore MHVB multiscreen plates (Cat# MHVBN4550) by making the following sequential additions to duplicate wells: (i) 100 μl/well of binding buffer containing 1.5 mM $MnCl_2$; (ii) 10 μl/well $^{125}$I-VCAM-Ig in binding buffer (final assay concentration<500 pM); (iii) 1.5 μl/well test compound or DMSO alone; (iv) 38 μl/well RPMI-8866 cell suspension (1.25×10$^6$ cells/well). The plates were incubated at room temperature for 45 minutes on a plate shaker at 200 rpm, filtered on a vacuum box, and washed on the same apparatus by the addition of 100 μL of binding buffer containing 1 mM $MnCl_2$. After insertion of the multiscreen plates into adapter plates (Packard, Meriden, Conn., cat# 6005178), 100 μL of Microscint-20 (Packard cat# 6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine- the level of binding corresponding to 100% inhibition. Percent inhibition was then calculated for each test well and the $IC_{50}$ was determined from a ten point titration using a validated four parameter fit algorithm.

What is claimed is:
1. A compound of formula Ia:

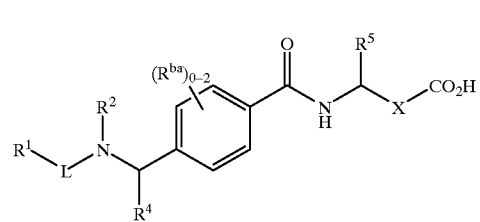

Ia wherein
X is
 1) a bond, or
 2) $C(R^7)(R^8)$;
L is
 1) —$S(O)_2$;
$R^1$ is
 1) Cy, or
 2) Cy-$C_{1-10}$alkyl,
wherein alkyl is optionally substituted with one to four substituents independently selected from $R^a$; and Cy is optionally substituted with one to four substituents independently selected from $R^b$; or
 $R^1$-L is
  4-[N'-(2-methylphenyl)ureido]phenylacetyl;
$R^2$ is
 1) H or
 2) $C_{1-5}$alkyl;
$R^4$ is
 1) H or
 2) $C_{1-5}$alkyl;
$R^5$ is
 1) $C_{1-10}$alkyl,
 2) Cy-$(Cy^1)_p$,
 3) Cy-$(Cy^1)_p$-$C_{1-10}$alkyl,
wherein alkyl is optionally substituted with one to four substituents independently selected from $R^a$; and Cy and $Cy^1$ are optionally substituted with one to four substituents independently selected from $R^b$;
$R^7$ is
 1) hydrogen, or
 2) $C_{1-3}$alkyl;
$R^8$ is
 1) hydrogen;
$R^a$ is
 1) —$CF_3$;
 2) —$OR^d$,
 3) —$NO_2$,
 4) halogen
 5) —$S(O)_mR^d$,
 6) —$CR^d(N$—$OR^e)$,
 7) —$S(O)_2OR^d$,
 8) —$S(O)_mNR^dR^e$,
 9) —$NR^dR^e$,
 10) —$O(CR^fR^g)_nNR^dR^e$,
 11) —$C(O)R^d$,
 12) —$CO_2R^d$, 13) —CO$_2$(CR$^f$R$^g$)$_n$CONR$^d$R$^e$,
14) —OC(O)R$^d$,
15) —CN,
16) —C(O)NR$^d$R$^e$,
17) —NR$^d$C(O)R$^e$,
18) —OC(O)NR$^d$R$^e$,
19) —NR$^d$C(O)OR$^e$, or
20) —NR$^d$C(O)NR$^d$R$^e$;

R$^b$ is
1) a group selected from R$^a$,
2) C$_{1-10}$ alkyl,
3) C$_{2-10}$ alkenyl,
4) C$_{2-10}$ alkynyl,
5) Cy, or
6) Cy-C$_{1-10}$ alkyl, wherein alkyl, alkenyl, alkynyl, and Cy are optionally substituted with a group independently selected from R$^c$;

substituted with a group independently selected from R$^c$;

R$^c$ is
1) halogen,
2) amino,
3) carboxy,
4) C$_{1-4}$alkyl,
5) C$_{1-4}$alkoxy,
6) aryl,
7) aryl C$_{1-4}$alkyl, or
8) aryloxy;

R$^d$ and R$^e$ are independently selected from the group consisting of
1) hydrogen,
2) C$_{1-10}$alkyl,
3) C$_{2-10}$alkenyl,
4) C$_{2-10}$alkynyl,
5) Cy, and
6) Cy C$_{1-10}$alkyl, wherein alkyl, alkenyl, alkynyl and Cy is optionally substituted with one to four substituents independently selected from R$^c$;

R$^f$ and R$^g$ are independently selected from hydrogen, C$_{1-10}$alkyl, Cy and Cy C$_{1-10}$alkyl;

R$^{ba}$ is
1) halogen,
2) C$_{1-3}$alkyl, or
3) C$_{1-3}$alkoxy;

Cy and Cy$^1$ are independently cycloalkyl or aryl;

m 0, 1 or 2;

n integer from 1 to 10;

p is 0 or 1; or a pharmaceutically acceptable salt thereof.

2. A compound selected from the group consisting of:

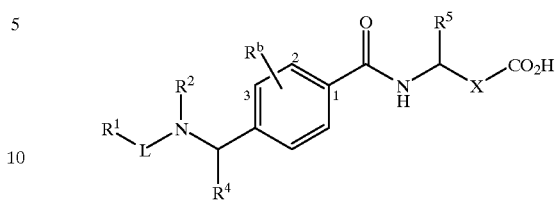

wherein
R$^2$ = R$^b$ = R$^4$ = H

| Ex | R$^1$—L | R$^5$ | X |
|---|---|---|---|
| 18 | benzoyl | 4-biphenylmethyl | — |
| 19 | phenylacetyl | 4-biphenylmethyl | — |
| 20 | 3,5-(diCl)-benzoyl | 4-biphenylmethyl | — |
| 21 | n-Bu—SO$_2$ | 4-biphenylmethyl | —. |

3. A compound of claim 1 having the formula Ib:

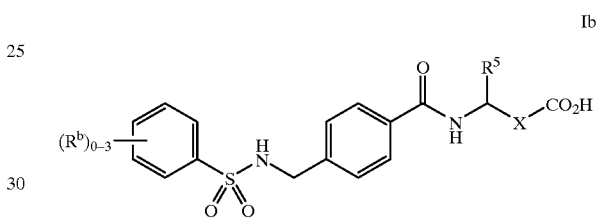

wherein
X is
1) a bond, or
2) CH$_2$;
R$^5$ is
1) C$_{1-5}$alkyl,
2) Cy-(Cy$^1$)$_p$,
3) Cy-(Cy$^1$)$_p$-C$_{1-3}$alkyl,
wherein Cy and Cy$^1$ are optionally substituted with one to two substituents independently selected from R$^b$;
Cy and Cy$^1$ are independently aryl;
R$^b$ is as defined in claim 1.

4. A compound of claim 1 having the formula Ic:

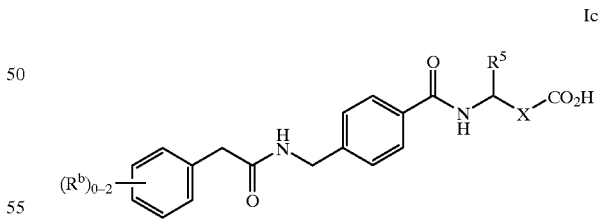

X is
1) a bond, or
2) CH$_2$;
R$^5$ is
1) C$_{1-5}$alkyl,
2) Cy-(Cy$^1$)$_p$,
3) Cy-(Cy$^1$)$_p$-C$_{1-3}$alkyl,
wherein Cy and Cy$^1$ are optionally substituted with one to two substituents independently selected from R$^b$;
Cy and Cy$^1$ are independently aryl;

$(R^b)_{0-2}$ represents 4-[N'-(2-methylphenyl)ureido].

5. A compound of claim 1 selected from the group consisting of:

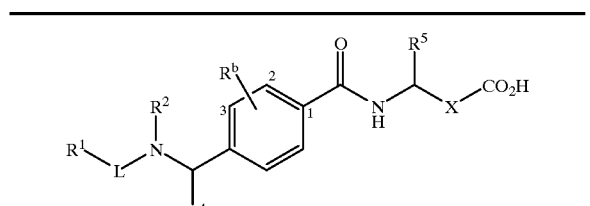

| Ex | $R^1$—L | $R^5$ | X |
|---|---|---|---|
| $R^2=R^b=R^4=H$ | | | |
| 1 | 2-MPUPA[a] | n-butyl | — |
| 2 | 2-MPUPA | benzyl | — |
| 3 | 2-MPUPA | phenyl* | — |
| 4 | 2-MPUPA | 4-biphenylmethyl | — |
| 5 | 2-MPUPA | methyl* | $CH_2$ |
| 6 | 2-MPUPA | benzyl* | $CH_2$ |
| 7 | 2-MPUPA | isobutyl* | $CH_2$ |
| 8 | 2-MPUPA | phenyl* | $CH_2$ |
| 9 | 2-MPUPA | H | $CH(CH_3)$* |
| 10 | 3,5-(diCl)—Ph—$SO_2$ | n-butyl | — |
| 11 | 3,5-(diCl)—Ph—$SO_2$ | benzyl | — |
| 12 | 3,5-(diCl)—Ph—$SO_2$ | phenyl* | — |
| 13 | 3,5-(diCl)—Ph—$SO_2$ | 4-biphenylmethyl | — |
| 14 | 3,5-(diCl)—Ph—$SO_2$ | phenyl* | $CH_2$ |
| 15 | 3,5-(diCl)—Ph—$SO_2$ | benzyl* | $CH_2$ |
| 16 | 3,5-(diCl)—Ph—$SO_2$ | isobuty*l | $CH_2$ |
| 17 | 3,5-(diCl)—Ph—$SO_2$ | benzyl# | — |
| 18 | benzoyl | 4-biphenylmethyl | — |
| 19 | phenylacetyl | 4-biphenylmethyl | — |
| 20 | 3,5-(diCl)-benzoyl | 4-biphenylmethyl | — |
| 21 | n-Bu—$SO_2$ | 4-biphenylmethyl | — |
| 22 | 3-(CN)—Ph—$SO_2$ | 4-biphenylmethyl | — |
| 23 | 3-(F)—Ph—$SO_2$ | 4-biphenylmethyl | — |
| 24 | 4-(OMe)—Ph—$SO_2$ | 4-biphenylmethyl | — |
| 25 | 3-($CH_3$)—Ph—$SO_2$ | 4-biphenylmethyl | — |
| 26 | 3-(Cl)—Ph—$SO_2$ | 4-biphenylmethyl | — |
| 27 | Ph—$SO_2$ | 4-biphenylmethyl | — |
| 28 | 4-(F)—Ph—$SO_2$ | 4-biphenylmethyl | — |
| 29 | 3-(Me)—Ph—$SO_2$ | 4-biphenylmethyl | — |
| 30 | 3,4-(di$CH_3$)—Ph—$SO_2$ | 4-biphenylmethyl | — |
| 31 | 4-(O$CH_3$)—Ph—$SO_2$ | 4-biphenylmethyl | — |
| 32 | 1-Me-4-imidazolyl-$SO_2$ | 4-biphenylmethyl | — |
| 33 | 4-(Cl)—Ph—$SO_2$ | 4-biphenylmethyl | — |
| 34 | 3,4-(diCl)—Ph—$SO_2$ | 4-biphenylmethyl | — |
| 35 | 2,3,4-(triF)-Ph—$SO_2$ | 4-biphenylmethyl | — |
| 36 | 2-(Cl)—Ph—$SO_2$ | 4-biphenylmethyl | — |
| 37 | 3-(Cl)-4-(F)—Ph—$SO_2$ | 4-biphenylmethyl | — |
| 38 | 2-thienyl-$SO_2$ | 4-biphenylmethyl | — |
| 39 | 2-(COOH)—Ph—$SO_2$ | 4-biphenylmethyl | — |
| 40 | 5-(Cl)-2-thienyl-$SO_2$ | 4-biphenylmethyl | — |
| 41 | 3,5-(diCl)—Ph—CO— | 4-biphenylmethyl | — |
| 43 | 3,5-(diCl)—Ph—$SO_2$ | 4-fluorobenzyl | — |
| 44 | 3-F—Ph—$SO_2$ | 4-fluorobenzyl | — |
| 45 | 3,5-(diCl)—Ph—$SO_2$ | 4-iodobenzyl | — |
| 46 | 3,5-(diCl)—Ph—$SO_2$ | 2'-cyanobiphenyl-methyl | — |
| 47 | 3,5-(diCl)—Ph—$SO_2$ | 2'-methoxybiphenylmethyl | — |
| 48 | 3,5-(diCl)—Ph—$SO_2$ | 4'-t-butylbiphenylmethyl | — |
| 49 | 3,5-(diCl)—Ph—$SO_2$ | 3'-methoxybiphenylmethyl | — |
| 50 | 3,5-(diCl)—Ph—$SO_2$ | 4'-methoxybiphenylmethyl | — |
| 51 | 3,5-(diCl)—Ph—$SO_2$ | 4'-methylthiobiphenylmethyl | — |
| 52 | 3,5-(diCl)—Ph—$SO_2$ | 2'-formylbiphenylmethyl | — |
| 53 | 3,5-(diCl)—Ph—$SO_2$ | 3'-acetamidobiphenylmethyl | — |
| 54 | 3,5-(diCl)—Ph—$SO_2$ | 4-(2-thienyl)benzyl | — |
| 55 | 3,5-(diCl)—Ph—$SO_2$ | 4-(3-chloro-2-thienyl)benzyl | — |
| 56 | 3,5-(diCl)—Ph—$SO_2$ | 4-(3-thienyl)benzyl | — |
| 57 | 3,5-(diCl)—Ph—$SO_2$ | 4-(2-naphthyl)benzyl | — |
| 58 | 3,5-(diCl)—Ph—$SO_2$ | 2'-cyanobiphenylmethyl (D isomer) | — |

-continued

| Ex | $R^1$—L | $R^5$ | X |
|---|---|---|---|
| 63 | 3,5-(diCl)—Ph—$SO_2$ | 4-(3-methyl-1,2,4-oxadiazol-5-yl)benzyl | — |
| 66 | 3,5-(diCl)—Ph—$SO_2$ | 4-(1-pyrrolidinecarbonyloxy)-benzyl | — |
| 67 | 3,5-(diCl)—Ph—$SO_2$ | 4-(2-ethoxyethoxy)benzyl | — |
| 68 | 3,5-(diCl)—Ph—$SO_2$ | 4-(t-butoxycarbonyloxy)-benzyl | — |
| 69 | 3,5-(diCl)—Ph—$SO_2$ | 4-(t-butoxy)benzyl | — |
| $R^b=R^4=H$; $R^2=CH_3$ | | | |
| 42 | 3,5-(diCl)—Ph—$SO_2$ | 4-biphenylmethyl | — |
| $R^2=R^4=H$; $R^b$ = 3-F (Ex. 59), 3-OMe (Ex. 61), 2-Me (Ex. 62) | | | |
| 59 | 3,5-(diCl)—Ph—$SO_2$ | 4-biphenylmethyl | — |
| 61 | 3,5-(diCl)—Ph—$SO_2$ | 4-biphenylmethyl | — |
| 62 | 3,5-(diCl)—Ph—$SO_2$ | 4-biphenylmethyl | — |
| $R^2=R^b=H$; $R^4=CH_3$ | | | |
| 64 | 3,5-(diCl)—Ph—$SO_2$ | 4-biphenylmethyl | — |
| 65 | 3,5-(diCl)—Ph—$SO_2$ | 2'-methoxybiphenylmethyl | — |
| 70 | 3-CN—Ph$SO_2$ | 2'-cyanobiphenylmethyl | — |

[a]2-MPUPA = 4-(N'-(2-methylphenyl)ureido)phenylacetyl.

6. A method for inhibiting cell adhesion in a mammal which comprises administering to said mammal an therapeutically effective amount of a compound of claim 1.

7. A method for the treatment of diseases, disorders, conditions or symptoms mediated by cell adhesion in a mammal which comprises administering to said mammal an therapeutically effective amount of a compound of claim 1.

8. A method for the treatment of asthma in a mammal which comprises administering to said mammal a therapeutically effective amount of a compound of claim 1.

9. A method for the treatment of allergic rhinitis in a mammal which comprises administering to said mammal a therapeutically effective amount of a compound of claim 1.

10. A method for the treatment of multiple sclerosis in a mammal which comprises administering to said mammal a therapeutically effective amount of a compound of claim 1.

11. A method for the treatment of atherosclerosis in a mammal which comprises administering to said mammal a therapeutically effective amount of a compound of claim 1.

12. A method for the treatment of inflammation in a mammal which comprises administering to said mammal an therapeutically effective amount of a compound of claim 1.

13. A method for the treatment of inflammatory bowel disease in a mammal which comprises administering to said mammal a therapeutically effective amount of a compound of claim 1.

14. A pharmaceutical composition which comprises a compound of claim 1 and a pharmaceutically acceptable carrier thereof.

* * * * *